(12) United States Patent
Zhang et al.

(10) Patent No.: US 11,939,399 B2
(45) Date of Patent: Mar. 26, 2024

(54) SYNTHETIC PEPTIDE SP4 AND USE THEREOF

(71) Applicant: TAIAN CITY QIHANG BIOTECHNOLOGY CO., Feicheng (CN)

(72) Inventors: Wanqin Zhang, Feicheng (CN); Yintian Li, Feicheng (CN); Xuewen Ji, Feicheng (CN); Limei Zhao, Feicheng (CN)

(73) Assignee: TAIAN CITY QIHANG BIOTECHNOLOGY CO., Feicheng (CN)

( * ) Notice: Subject to any disclaimer, the term of this patent is extended or adjusted under 35 U.S.C. 154(b) by 0 days.

(21) Appl. No.: 17/656,347

(22) Filed: Mar. 24, 2022

(65) Prior Publication Data

US 2022/0332761 A1    Oct. 20, 2022

Related U.S. Application Data

(63) Continuation of application No. 16/762,470, filed as application No. PCT/CN2018/109931 on Oct. 12, 2018, now abandoned.

(30) Foreign Application Priority Data

Jul. 6, 2018   (CN) .......................... 201810739279.3

(51) Int. Cl.
   *C07K 7/08*     (2006.01)
   *A61P 35/00*    (2006.01)
   *A61K 38/00*    (2006.01)

(52) U.S. Cl.
   CPC ................ *C07K 7/08* (2013.01); *A61P 35/00* (2018.01); *A61K 38/00* (2013.01)

(58) Field of Classification Search
   None
   See application file for complete search history.

(56) References Cited

U.S. PATENT DOCUMENTS

2007/0237714 A1* 10/2007 Alvarez .......... G01N 33/57492
                                                          424/1.69

FOREIGN PATENT DOCUMENTS

CN     101270145 A     9/2008
CN     101314617 A    12/2008

OTHER PUBLICATIONS

Alberts et al. (Molecular Biology of the Cell. 4th edition, New York: Garland Science; 2002; retrieved from http://www.ncbi.nlm.nih.gov/books/NBK26917/ on Mar. 2, 2015, 10 pages) (Year: 2002).*
Wang et al. ('Scorpion venom induces glioma cell apoptosis in vitro and inhibits glioma tumor growth in vivo' Journal of Neuro-Oncology v73 2005 pp. 1-7) (Year: 2005).*
Zhu, S. et al. "GenBank Accession No. ABR21077, Version ABR21077.1"; GenBank, Dec. 1, 2010, p. 1.
NCBI BLAST search seq id 1 (retrieved from https://blast.ncbi.nlm.nih.gov/Blast.cgi on Aug. 16, 2021, 15 pages). (Year: 2021).
Zeng, Xian-Chun et al.; "Identification and functional characterization of novel scorpion venom peptides with no disulfide bridges from Buthus marensii Karsch"; Peptides; Feb. 2004; vol. 25; pp. 143-150.

* cited by examiner

*Primary Examiner* — Ronald T Niebauer
(74) *Attorney, Agent, or Firm* — NKL Law; Allen Xue

(57) ABSTRACT

A synthetic peptide sp4 has an amino acid sequence shown in SEQ ID NO: 1. As the sole effective ingredient in the antitumor efficacy test, it has a significant inhibitory effect on both the tumor volume and tumor weight of human osteosarcoma MG-63 in nude mice and has a significant dose-effect and time-effect relationship. There is no difference between the relative tumor growth rate T/C (%) of sp4 and that of the positive control group of Paclitaxel. The safety of sp4 is that its maximal tolerated dose for intravenous administration is 700 mg/kgBW. Sp4 has clear targets of pharmacological effects, while having efficacy in vivo, it also has an inhibitory effect on tumor telomerase, has an arrest on G1 phase of the tumor cell cycle, and inhibits the high expressions of tumor PD-L1 and CD47. The present disclosure relates to multiple uses of sp4, especially in the preparation of a class of antitumor drugs.

12 Claims, 24 Drawing Sheets

Specification includes a Sequence Listing.

VIS 1 Results

| Pk# | RT | Name | Height | Area | ESTD Conc/nmol | Calc% |
|---|---|---|---|---|---|---|
| 1 | 6.193 | Ser | 466493 | 8314408 | 4.450 | 467.679 |
| 3 | 9.893 | Gly | 133350 | 2465865 | 1.753 | 131.681 |
| 4 | 10.673 | Ala | 115052 | 2453264 | 1.754 | 156.237 |
| 6 | 15.593 | Ile | 156860 | 4704615 | 3.401 | 446.244 |
| 7 | 16.753 | Leu | 148043 | 5327072 | 3.615 | 474.321 |
| 8 | 18.807 | Phe | 247549 | 5613282 | 3.403 | 562.232 |
| 9 | 22.120 | NH3 | 23924 | 697487 | 0.673 | 11.440 |
| Totals | | | 1291271 | 29575993 | 19.050 | |

VIS 2 Results

| Pk# | RT | Name | Height | Area | ESTD Conc/nmol | Calc% |
|---|---|---|---|---|---|---|
| 1 | 7.653 | Pro | 32471 | 420957 | 1.754 | 201.871 |
| Totals | | | 32471 | 420957 | 1.754 | |

Fig. 1A Continued

|  | nmol/20μl | AminoAcid Composition |
|---|---|---|
| Asp | — | — |
| Thr | — | — |
| Ser | 4.450 | 2.54 |
| Glu | — | — |
| Gly | 1.753 | 1.00 |
| Ala | 1.754 | 1.00 |
| Cys | — | — |
| Val | — | — |
| Met | — | — |
| Ile | 3.401 | 1.94 |
| Leu | 3.615 | 2.06 |
| Tyr | — | — |
| Phe | 3.403 | 1.94 |
| Lys | — | — |
| His | — | — |
| Arg | — | — |
| Pro | 1.754 | 1.00 |

Fig. 1B

SEQ ID NO: 1
Dissolution method: 1 mg dissolved in 1 ml of pure water
Product Name   :   FG-12
Lot No.        :   NJP80036-170518
Column         :   4.6*250mm, SinoChrom ODS-BP 5um
Solvent A      :   0.1% trifluoroacetic in 100% acetonitrile
Solvent B      :   0.1% trifluoroacetic in 100% water
Gradient                       A           B
                 0.01min      38%         62%
                 25min        63%         37%
                 25.1min      100%        0%
                 30min                    STOP
Flow rate      :   1.0ml/min
Wavelength     :   220nm
Volume         :   10 μl

| Peak No. | Ret Time | Height    | Area        | Conc.   |
|----------|----------|-----------|-------------|---------|
| 1        | 9.687    | 716.669   | 9035.043    | 0.1057  |
| 2        | 10.243   | 7499.993  | 45164.742   | 0.5284  |
| 3        | 10.435   | 760040.438| 8427603.000 | 98.5992 |
| 4        | 10.893   | 5395.544  | 65534.488   | 0.7667  |

File analyzed: Data 001.LMD
Date analyzed: 18-May-2018
Model: 1nn0n_DSD
Analysis type: Manual analysis Ploidy Mode: First cycle is diploid Diploid: 100.00%
    Dip G1: 41.43 % at 53.23
    Dip G2: 14.29 % at 106.45
    Dip S: 44.29 %    G2/G1: 2.00
    %CV: 4.70

Control

File analyzed: Data 006.LMD
Date analyzed: 18-May-2018
Model: Inn0n_DSD
Analysis type: Manual analysis Ploidy Mode: First cycle is diploid Diploid: 100.00%
    Dip G1: 66.54 % at 60.56
    Dip G2: 9.69 % at 116.88
    Dip S: 23.76 %    G2/G1: 1.93
    %CV: 5.33 sp 200μm

File analyzed: Data 007.LMD
Date analyzed: 18-may-2018
Model: 1nn0n_DSD
Analysis type: Manual analysis Ploidy Mode: First cycle is diploid Diploid: 100.00%
    Dip G1: 65.79 % at 50.28
    Dip G2: 6.03 % at 100.56
    Dip S: 28.17 %    G2/G1: 2.00
    %CV: 5.18 sp4 100μM

File analyzed: Data 009.LMD
Date analyzed: 18-May-2018
Model: 1nn0n_DSD
Analysis type: Manual analysis Ploidy Mode: First cycle is diploid Diploid: 100.00%
  Dip G1: 62.32 % at 54.78
  Dip G2: 14.85% at 105.18
  Dip S: 22.82 %   G2/G1: 1.92
  %CV: 5.70 sp4 25μM

SEQUENCE LISTING

<160> NUMBER OF SEQ ID NOS: 1

<210> SEQ ID NO 1
<211> LENGTH: 12
<212> TYPE: PRT
<213> ORGANISM: Sequoia sempervirens

<400> SEQUENCE: 1

Phe Leu Phe Ser Leu Ile Pro Ser Ala Ile Ser Gly
1               5                   10

SYNTHETIC PEPTIDE SP4 AND USE THEREOF

CROSS-REFERENCE TO RELATED APPLICATIONS

This application is a continuation application of U.S. patent application Ser. No. 16/762,470, filed May 7, 2020, which is a U.S. national entry of PCT international application no. PCT/CN2018/109931, filed Oct. 12, 2018, which claims the benefit of priority from Chinese patent application no. 201810739279.3, filed Jul. 6, 2018, the contents of which are incorporated herein by reference in their entireties.

INCORPORATION OF SEQUENCE LISTING

This application contains a sequence listing submitted in Computer Readable Form (CRF). The CFR file containing the sequence listing entitled "PA128-0079CON_ST25.txt", which was created on Mar. 24, 2022, and is 529 bytes in size. The information in the sequence listing is incorporated herein by reference in its entirety.

TECHNICAL FIELD

The present disclosure belongs to the technical field of biomedicines, relates to a synthetic peptide sp4 (Synthetic Peptide-4) and uses thereof, in particular to uses in preparing novel anti-tumor drugs.

BACKGROUND ART

Cancer is a serious threat to human health and life. Osteosarcoma (OS) is a type of most common primary bone malignancy and a highly malignant mesenchymal tumor. It often occurs in adolescents below the age of 21 and children. Osteosarcoma presents invasive growth locally and grows rapidly, and it is featured by a high degree of malignancy, proneness to metastasis, poor limb salvage treatment effect, high disability and mortality, etc. Chemotherapy is very important for the treatment of metastases lesions. At present, in clinical practices, cytotoxic antitumor drugs are mainly used, including combined use of Paclitaxel, Cisplatinum, Methotrexate (MTX), Adriamycin (ADM), Ifosfamide (IFO), etc., and the toxic and side effects bring great harm and pain to patients. Esophagus cancer is one of the common digestive system tumors, which is also treated by combined chemotherapy with high toxic and side effects. Polypeptide compounds are a category of important biologically active molecules. Chemical synthetic peptide sp4 is a small peptide synthesized by polypeptide solid-phase synthesis technology, which is processed by biotechnology, such as HPLC purification, mass spectrometry analysis and identification, provide quantitative data for the preparation, structural confirmation and quality research of sp4 drugs. So far, no similar chemical synthetic peptides and the uses thereof in anti-tumor drugs have been reported in the prior art.

SUMMARY OF THE INVENTION

The present disclosure discloses a chemical synthetic peptide sp4, whose amino acid sequence is shown in SEQ ID NO: 1. Compared with natural antitumor polypeptides, high-purity polypeptide monomers can be obtained by chemical synthesis. In the prior art, no similar compounds have been found.

The present disclosure further protects the uses of the synthetic peptide sp4 of any one of the following (1) to (8): (1) preventing and/or treating tumors; (2) inhibiting proliferation and/or growth and/or invasion of tumor cells; (3) enhancing anti-tumor immunoreaction; (4) inducing differentiation of tumor cells; (5) preparing anti-tumor drugs; (6) inhibiting the activity of tumor telomerase; (7) regulating tumor cell cycle; and (8) preparing products for regulating tumor cell cycle.

Further, for the use (6) of the synthetic peptide sp4, inhibiting the activity of tumor telomerase means the use as a tumor telomerase inhibitor peptide. The synthetic peptide sp4 has a strong inhibitory effect on telomerase activity in both tumor cell lines in vitro and tumor tissues in vivo.

Further, for the use (8) of the synthetic peptide sp4, preparing products for regulating tumor cell cycle means the use as a tumor cell cycle regulating drug. The synthetic peptide sp4 has a G1 phase arrest, which is possibly related to the inhibition of telomerase activity.

Further, the tumor is human osteosarcoma or human esophagus cancer. The human esophagus cancer includes malignant tumors of esophageal squamous epithelium and columnar epithelium.

The present disclosure further provides a biologically active molecular product whose active ingredient is the synthetic peptide sp4. Further, the only effective active ingredient of the product is the synthetic peptide sp4. The anti-tumor drugs using the synthetic peptide sp4 as effective active ingredient in the embodiments of the present disclosure have good effect. The sp4 has a definite antitumor target, and a form of single medication can be used, that is, as the only effective active ingredient, which has obvious curative effect.

Cytotoxic anti-tumor drugs are one of the important methods for the treatment of malignant tumors. In order to reduce the toxicity of cytotoxic anti-tumor drugs, a variety of combined medications are adopted. The present disclosure provides a non-cytotoxic chemical synthetic peptide sp4, which is a single drug, has significant curative effect, targets telomerase activity of tumor cell DNA telomeres, and involves in the cell cycle regulation. For the preclinical antitumor efficacy studies, in addition to investigation on the effect of test substance and its sensitivity to different types of tumors, special attention should be paid to the comparison of test results between the test substance and positive control drugs. In the present disclosure, in the in vitro anti-tumor activity screening test (cell counting kit-8, CCK-8), sp4 was co-cultured with MG-63 and Eca-109 cells for 72 hours, and the results showed that the inhibition rate of sp4 on MG-63 cells was 93.84%, while the inhibition rate on the Eca-109 cells was 73.58%, presenting an apparent dose-effect relationship. The in vivo test is a decisive indicator for evaluating the effectiveness of the test substance on the killing or inhibitory effect of specific types of tumor cells. The in vivo pharmacodynamic test of the present disclosure used subcutaneous human cancer xenograft tumor models in nude mice and measured the tumor-size every other day, to dynamically observe the growth of xenograft tumors. At the end of experiments, the tumor was weighed. The present disclosure found that sp4 had a significant inhibitory effect on volume and weight of subcutaneous human osteosarcoma MG-63 xenograft tumor of nude mice, presenting an apparent dose-effect and time-effect relationship; the relative tumor proliferation rate T/C (%) was 10.27±1.87, and the tumor growth inhibition rate was 88.31%. The statistical analysis shows that sp4 has a strong anti-tumor effect. In addition, the relative tumor proliferation rate T/C (%) of sp4 group was not significantly different from that of the positive control group Paclitaxel (P>0.05), which is one of the important indicators to evaluate whether the test substance sp4 is necessary to enter clinical trials. Regarding the safety of the present disclosure, the maximum tolerated dose is tested using an acute toxicity test. After intravenous injection of sp4 at a dose of 700 mg/kg BW to animals, no toxic reaction and death were observed within 24 hours, and no behavioral abnormalities and deaths were observed within 2 weeks. In the in vivo pharmacodynamic test, the weight gain of tumor-bearing nude mice in each treatment group was not different from that of the control group (P>0.05), and no death occurred, as shown in FIG. 15. The maximum tolerated dose of sp4 is shown in Tables 2 and 3.

After a treatment of human promyelocytic leukemia cell line HL-60 with different concentrations of sp4, the expression of cells in G0/G1 phase increased, and that in S phase and G2 phase decreased, presenting a G1 phase arrest and having a dose-effect relationship. In subcutaneous human osteosarcoma xenograft tumor models in nude mice, the sp4 high-dose and low-dose groups and the positive control Paclitaxel group also shows significant G1 phase arrest.

Telomere is a special structure located at the end of chromosome and can maintain cell division. Telomerase can catalyze the replication and extension of telomere DNA, leading to infinite division and proliferation of cancer cells. Anti-telomerase activity is one of the important targets for anti-tumor therapy. Sp4 has an apparent inhibitory effect on the telomerase activity of in vitro tumor cell lines and in vivo tumor tissues, both presenting an apparent dose-effect relationship.

Cell cycle is the basic process of cell life activity. Using flow cytometry to detect cell cycle, it shows that cells are blocked on G1 phase after treatment with sp4, suggesting that sp4 may involve in the regulation of tumor cell cycle through inhibition on the telomerase activity. The inhibition of telomerase activity increases the inhibitory activity of cyclin dependent kinase (CDK) inhibitors. CDK inhibitors compete with cyclin D1 to bind to CDK4, increase the inhibitory activity of CDK4 and prevent cells from entering the S phase from the G1 phase.

BRIEF DESCRIPTION OF THE DRAWINGS

FIG. 1A and FIG. 1B are the amino acid composition of sp4;

FIG. 5A is a inhibition rate of sp4 on proliferation activity in vitro of human esophagus cancer Eca109; FIG. 5B is a inhibition rate of sp4 on proliferation activity in vitro of human osteosarcoma MG63;

FIG. 14A: control group, FIG. 14B: 200 μM, FIG. 14C: 100 μM, FIG. 14D: 50 μM, FIG. 14E: 25 μM;

DETAILED DESCRIPTION

The following embodiments further explain the present disclosure, and set forth some details to facilitate an understanding of the present disclosure. However, the present disclosure can be implemented in many other ways than those described herein, so the present disclosure is not limited by the embodiments disclosed below.

Embodiment 1

Analysis of the amino acid composition of sp4:

10.2 mg of sample was weighed and dissolved in 7 mL of 6N HCl, and hydrolyzed for 22 hours under nitrogen protection condition at 110° C. After cooling, hydrolysate was transferred to a 10 mL volumetric flask and constant-volumed. 0.2 mL of solution was taken from the flask and blew dry with 55° C. nitrogen, and 1 mL distilled water was added and dried again and repeated three times. The dried product was dissolved in 1.2 mL of deionized water (pH was adjusted with 0.02 mol/L HCl) and mixed uniformity, filtered through a 0.45 μm filter membrane, and 20 μL solution was injected in a machine (Hitachi L-8900 Amino Acid Analyzer) for testing.

Test results:

| | | nmol/20 μL | Amino acid ratio |
|---|---|---|---|
| Ser | Serine | 4.450 | 2.54 |
| Gly | Glycine | 1.753 | 1.00 |
| Ala | Alanine | 1.754 | 1.00 |
| Ile | Isoleucine | 3.401 | 1.94 |
| Leu | Leucine | 3.615 | 2.06 |
| Phe | Phenylalanine | 3.403 | 1.94 |
| Pro | Proline | 1.754 | 1.00 |

Figure 1A:
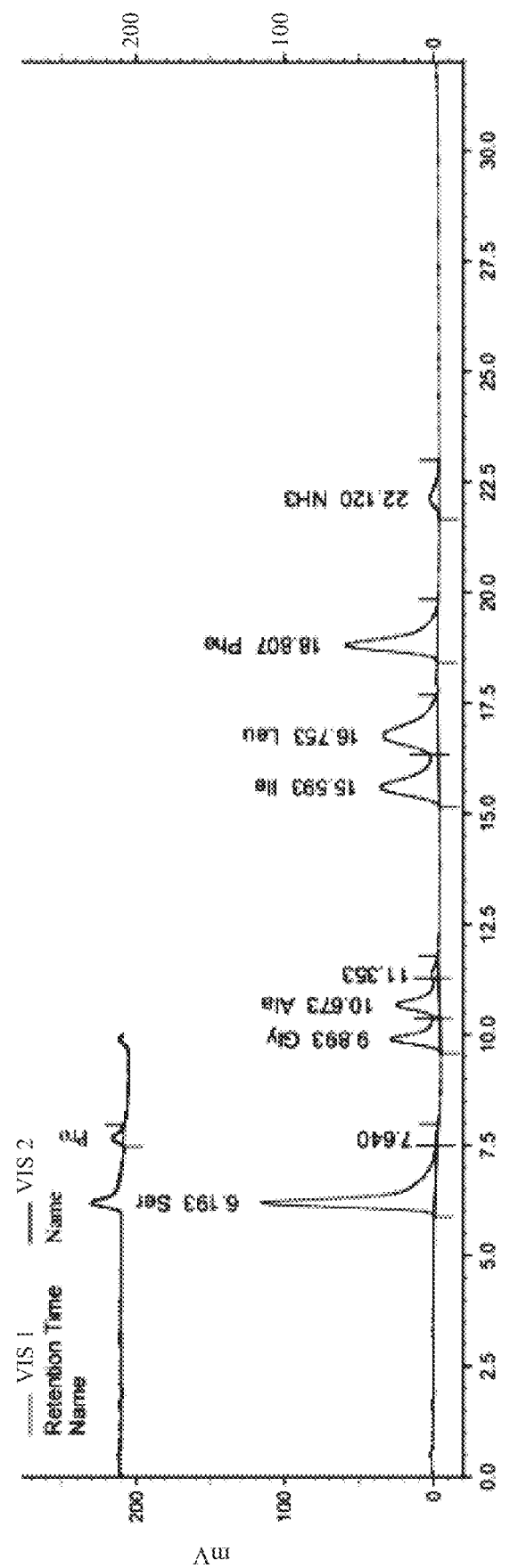

Sp4 is composed of 7 kinds amino acids of S, G, A, I, L, F and P, as shown in FIGS. 1A and B.

Embodiment 2

Figure 2:
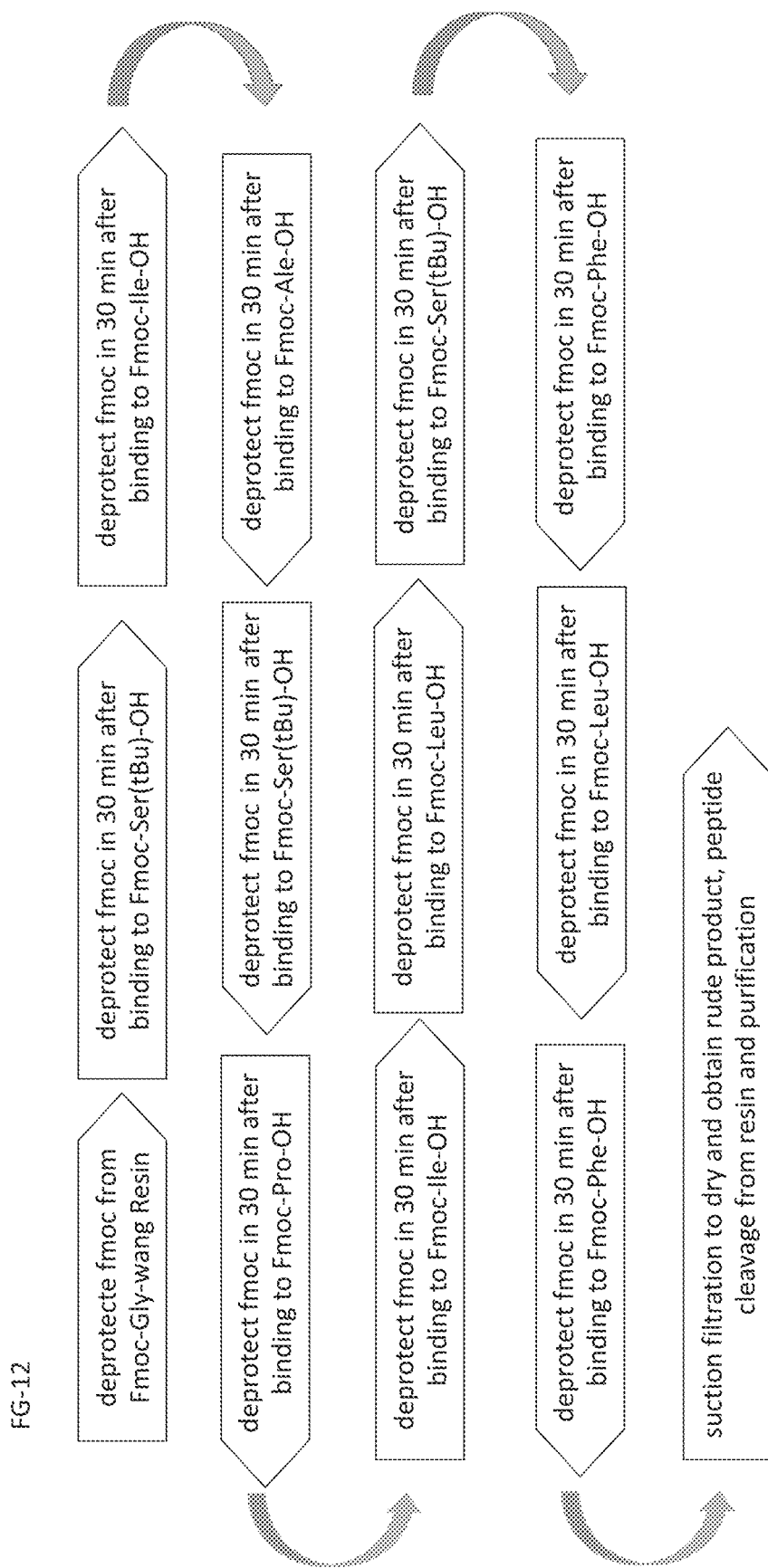
FIG. 2 illustrates a schematic diagram of a chemical synthesis of sp4.
Figure 3:
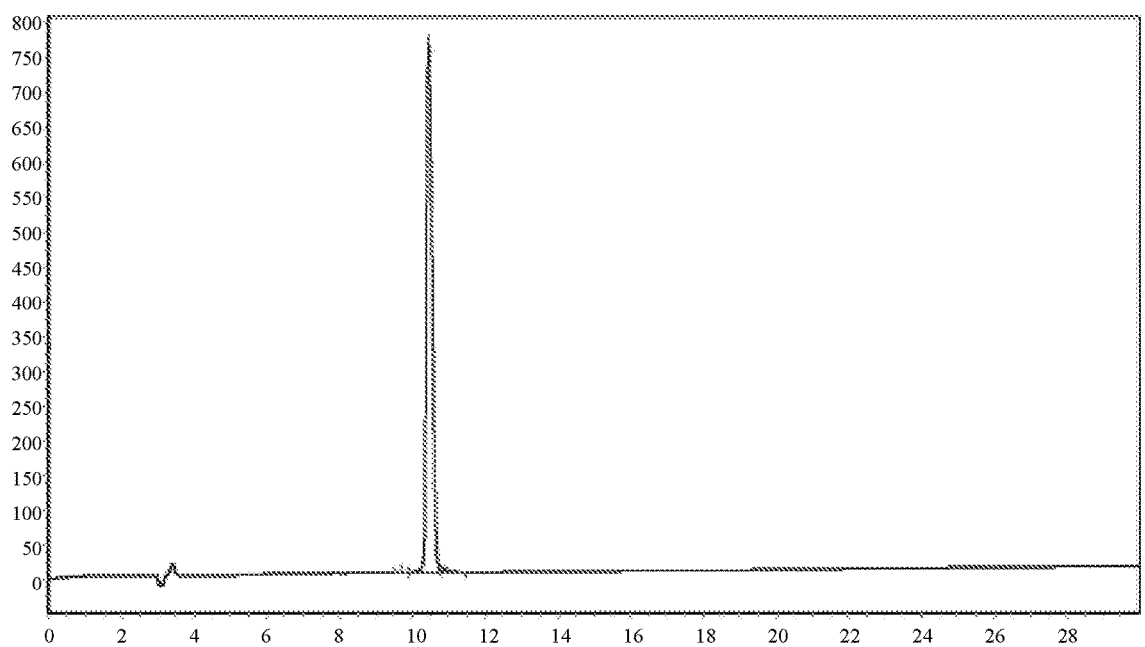
FIG. 3 illustrates a chromatographic result of sp4.
Figure 4:
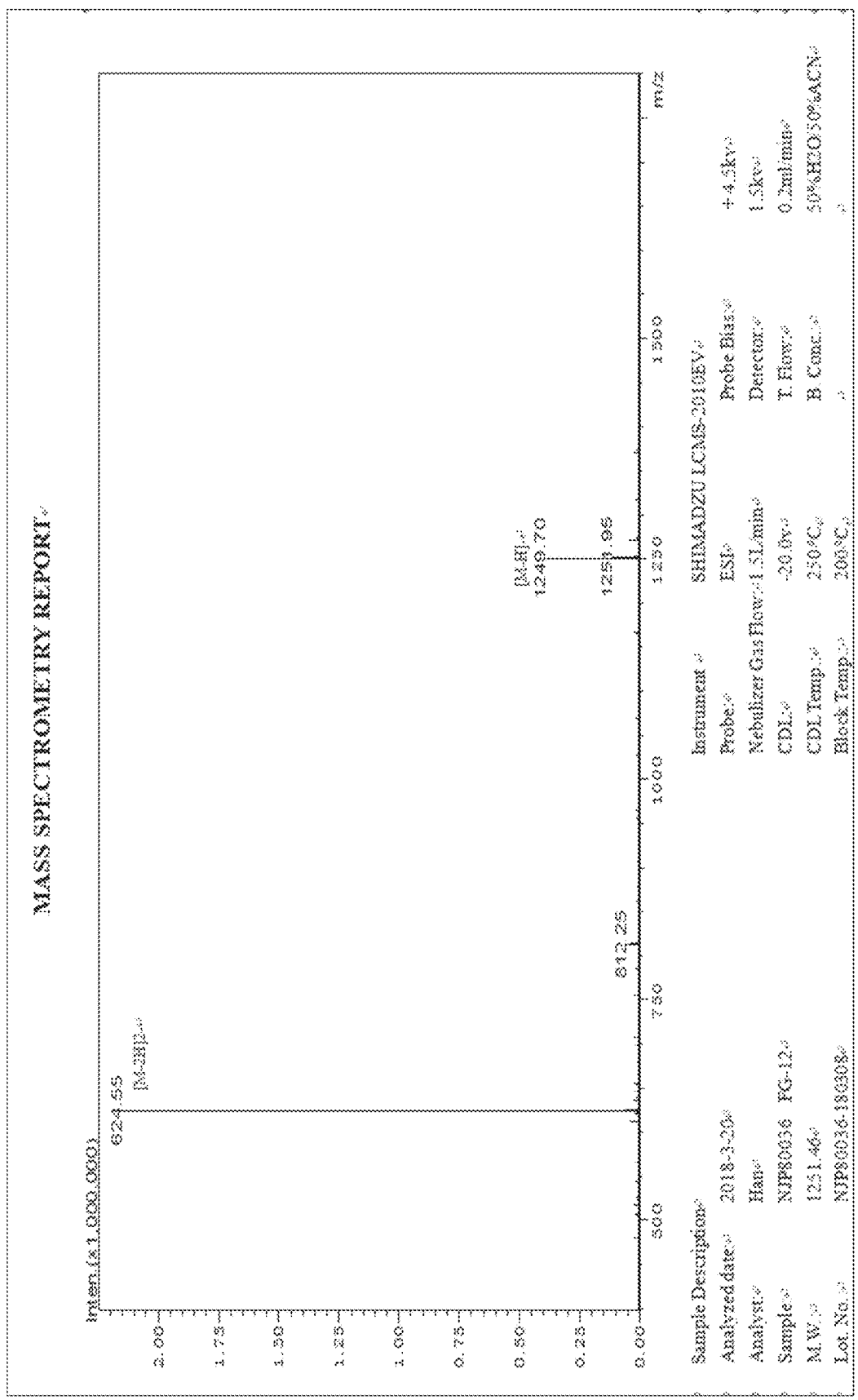
FIG. 4 illustrates a mass spectrum result of sp4.

Solid-phase chemical synthesis, purity testing and molecular weight of sp4:

Solid-phase chemical synthesis of sp4: The peptide Fmoc solid-phase synthesis technology was adopted, which is a process of repeatedly adding amino acids from the C-terminus to the N-terminus of the known polypeptide amino acid sequence. The process was shown in FIG. 2: firstly, covalently attaching the carboxyl group of a first amino acid at the C-terminus of the target polypeptide to the solid phase carrier (resin), and then using the amino group of this amino acid as the starting point for synthesis to have an acylation reaction with the carboxyl group of adjacent amino acid to form peptide bond. Repeating the above process until the synthesis of target polypeptide is completed, then cleaving the target polypeptide from the resin and removing the side chain protecting group contemporaneously. Finally, adding ice ether to precipitate the crude peptide, which is separated and purified by high-performance liquid chromatography, and then identified by mass spectrometry (see FIGS. 2-4).

Embodiment 3

Anti-tumor in vitro screening test (method of CCK-8) was used. This technique was provided by Nanjing OGpharmaceutical science and technology Co., Ltd. and cell viability detection kits of EnoGeneCell™ Counting Kit-8 (CCK-8) were used.

Figures 5A, 5B:
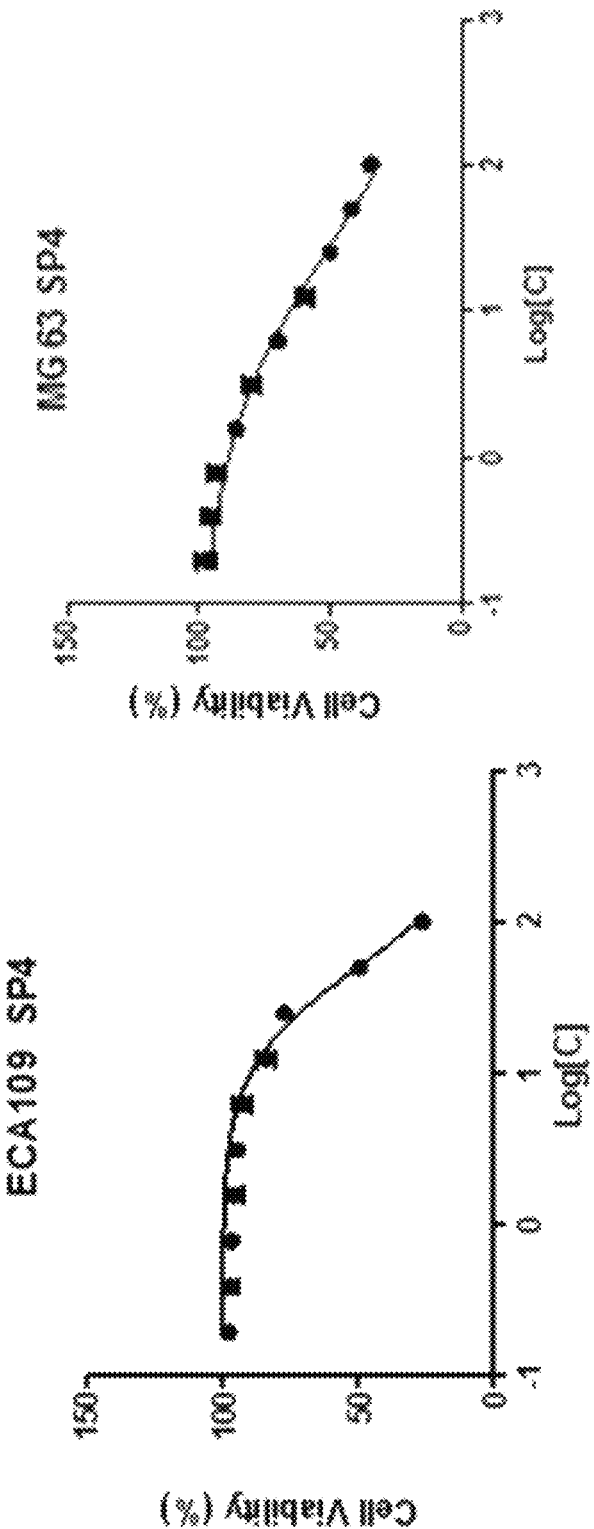
FIG. 5A and FIG. 5B illustrate a pharmacological effect in vitro of sp4.
Figure 6:
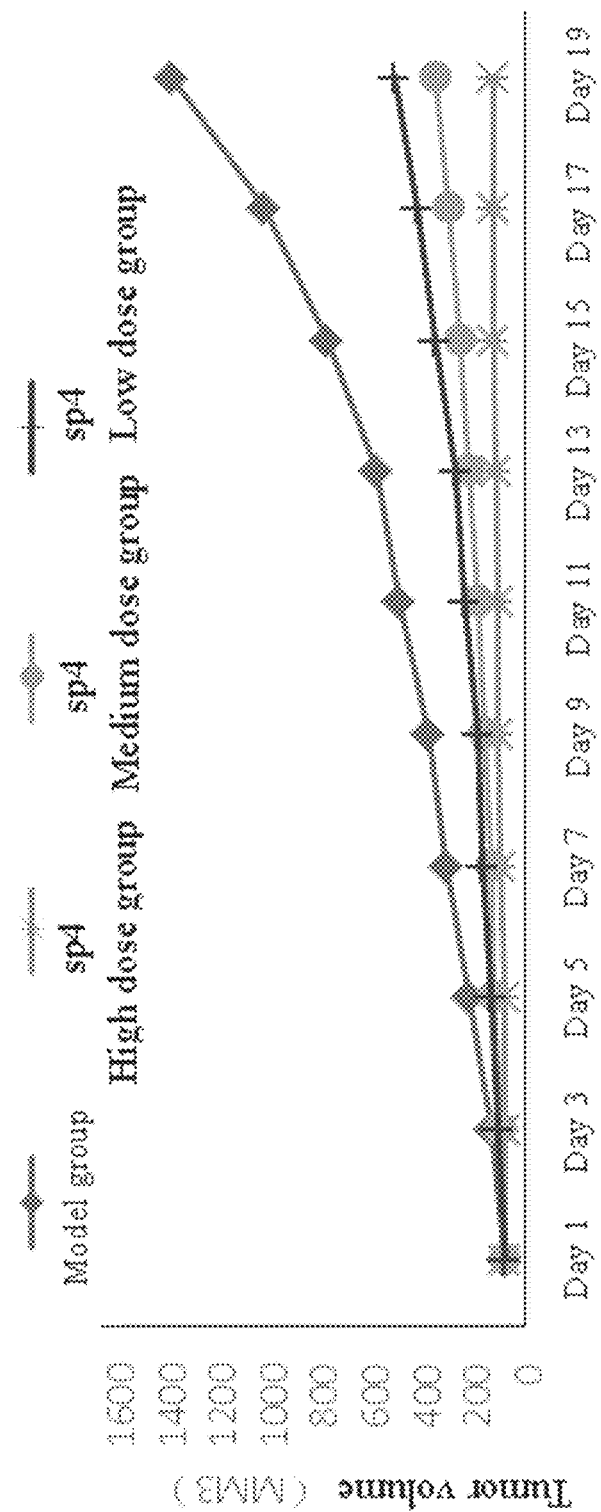
FIG. 6. illustrates in vivo antitumor effect of sp4: tumor growth curves.
Figure 7:
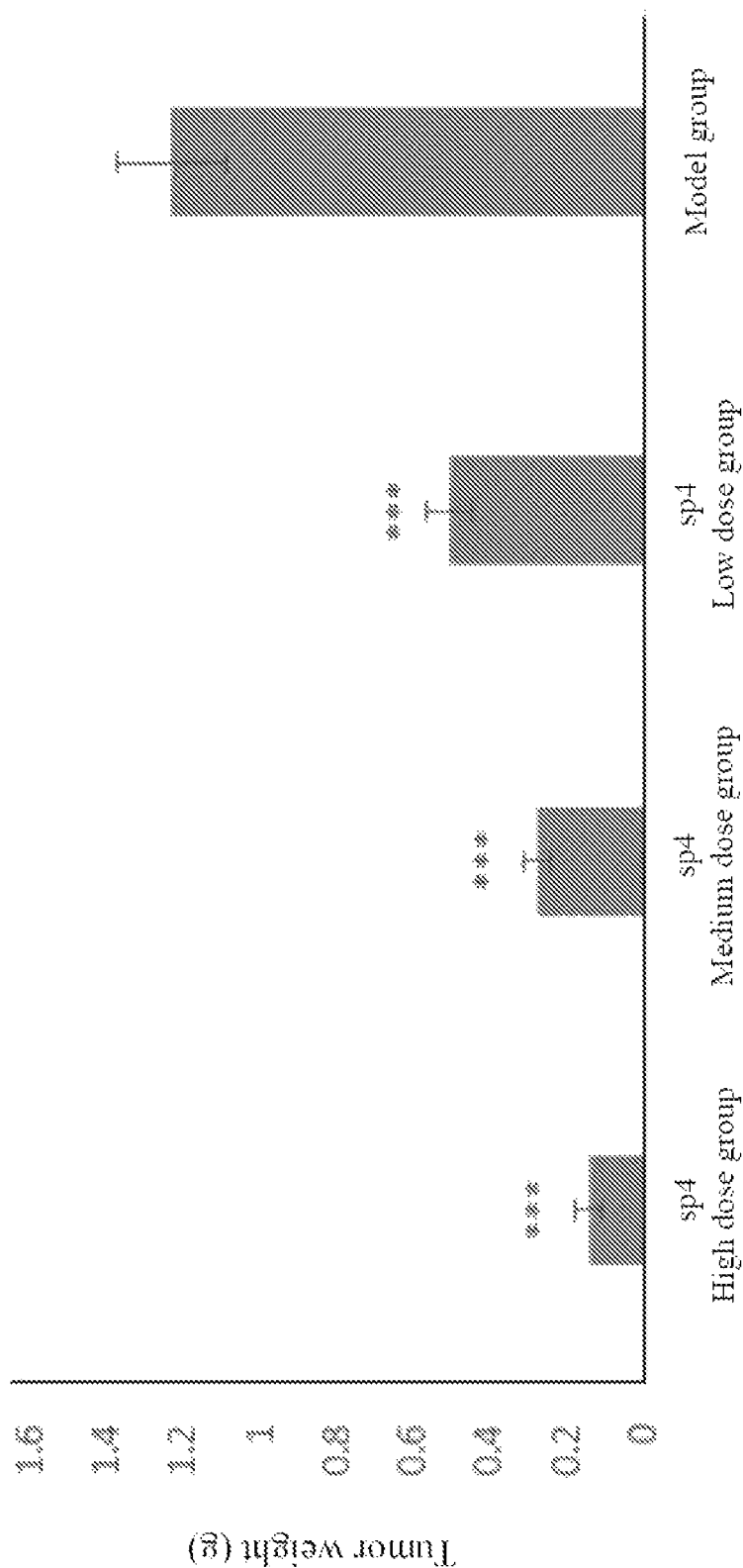
FIG. 7 illustrates in vivo antitumor effect of sp4: inhibitory effect on tumor weight of tumor-bearing nude mice; after treatment with different concentrations of sp4, the statistical difference in each group compared with the model group, wherein, * represents P<0.05,  represents P<0.01, * represents P<0.001.
Figure 8:
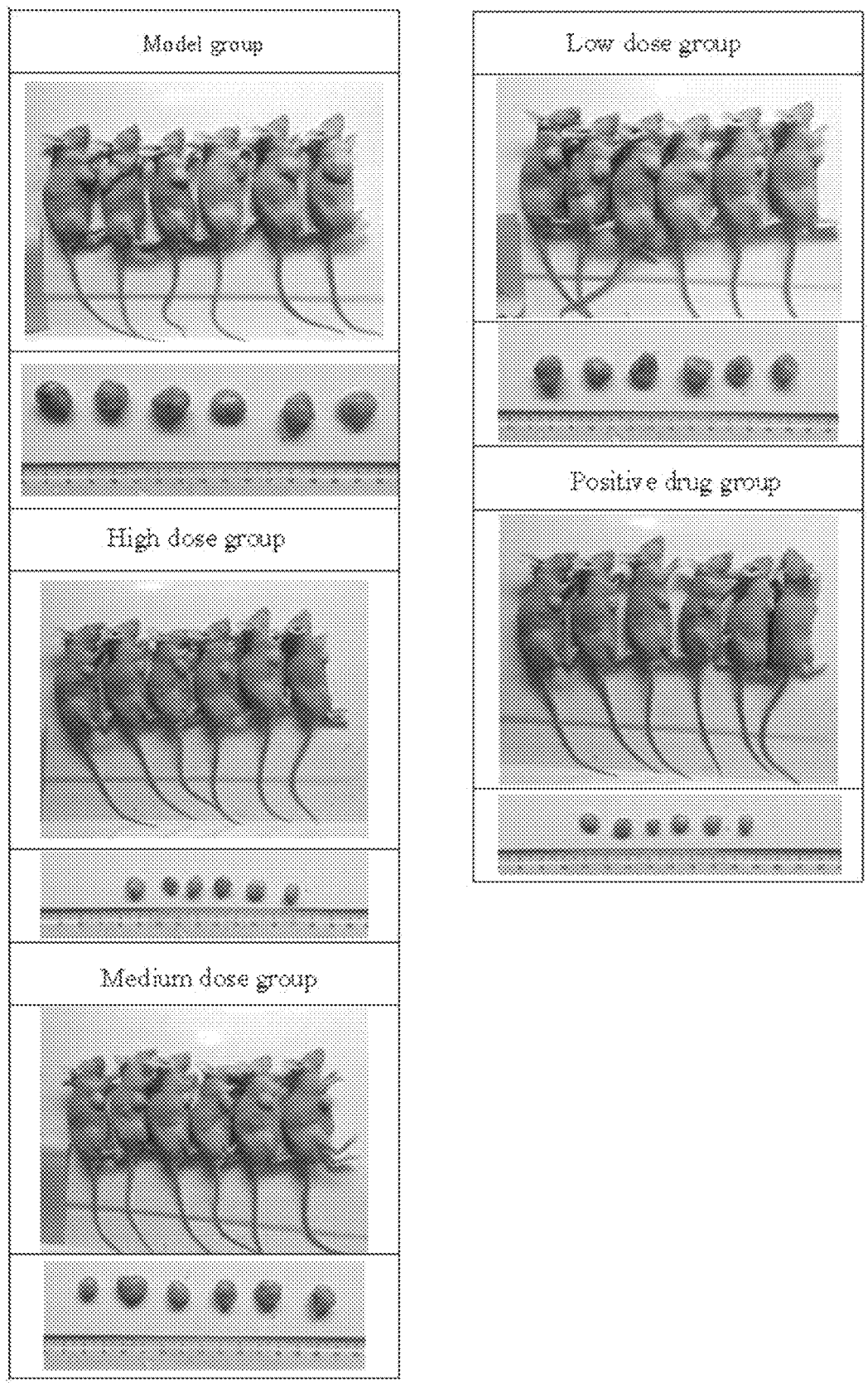
FIG. 8 illustrates images of anti-tumor effect evaluation experiments with sp4 via tail vein injection; in the figure, shooting conditions for measuring tumor volume are the same, and the tumor volume in each group is shown in FIG. 8 according to the scale.
Figure 9:
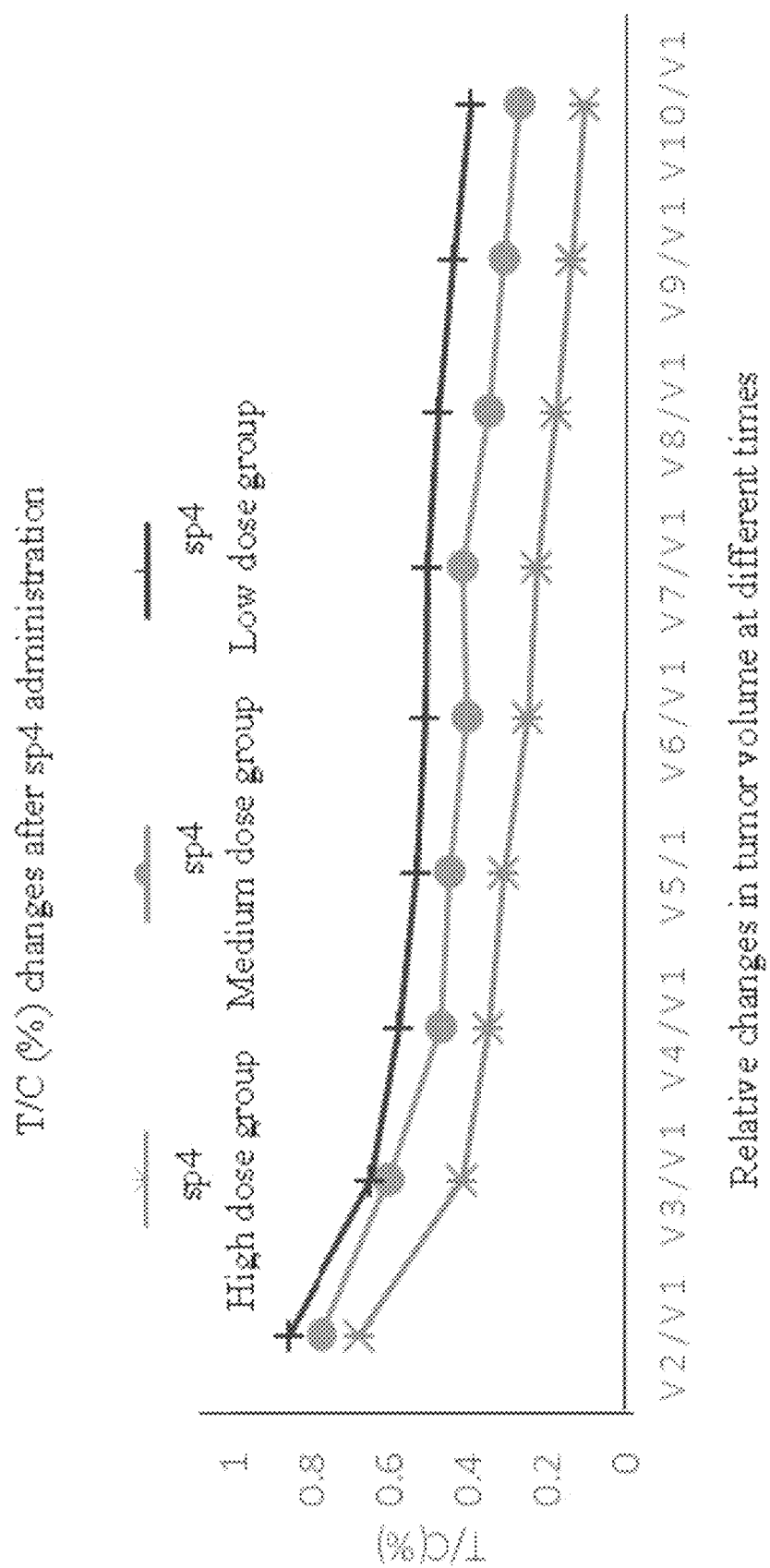
FIG. 9 illustrates in vivo anti-tumor effect of sp4: relative tumor proliferation rate T/C (%); according to national FDA guidelines, for cytotoxic anti-tumor drugs, pharmacodynamic evaluation criteria of nude mice xenograft models is: T/C (%)>40% indicates ineffective; T/C (%)≤40% and P<0.05 with statistical processing indicates effective. The results show that sp4 drug appears to be effective on the $19^{th}$ day of treatment at low doses, and be effective on the $15^{th}$ day of treatment at medium doses, and be effective on the $7^{th}$ day of treatment at high doses.
Figure 10:
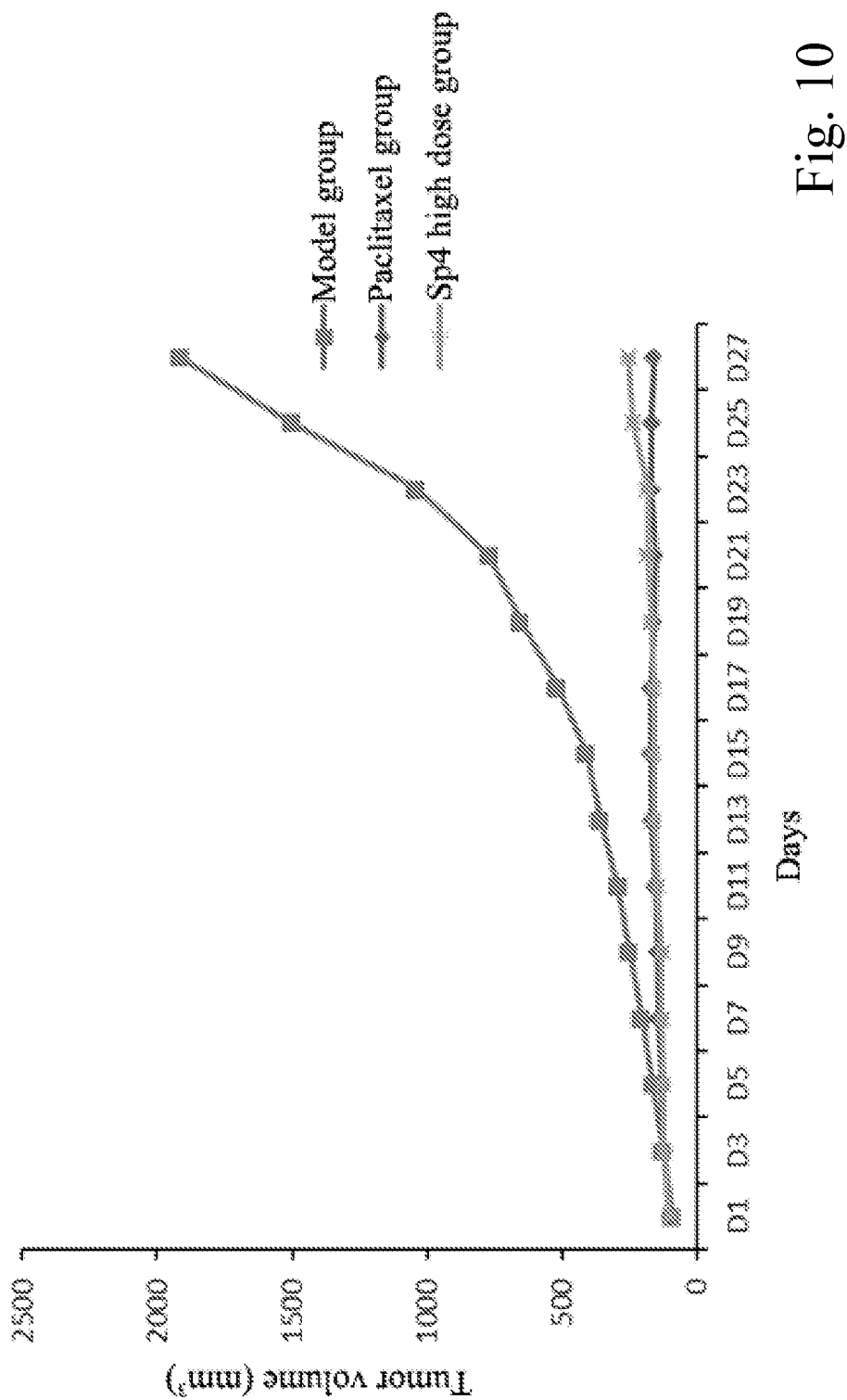
FIG. 10 illustrates in vivo anti-tumor effect of sp4 compared with positive control Paclitaxel: tumor growth curves of sp4 and Paclitaxel. There is no significant difference between the two (P>0.05), the ordinate shows tumor volume and the abscissa shows administration days.
Figure 11:
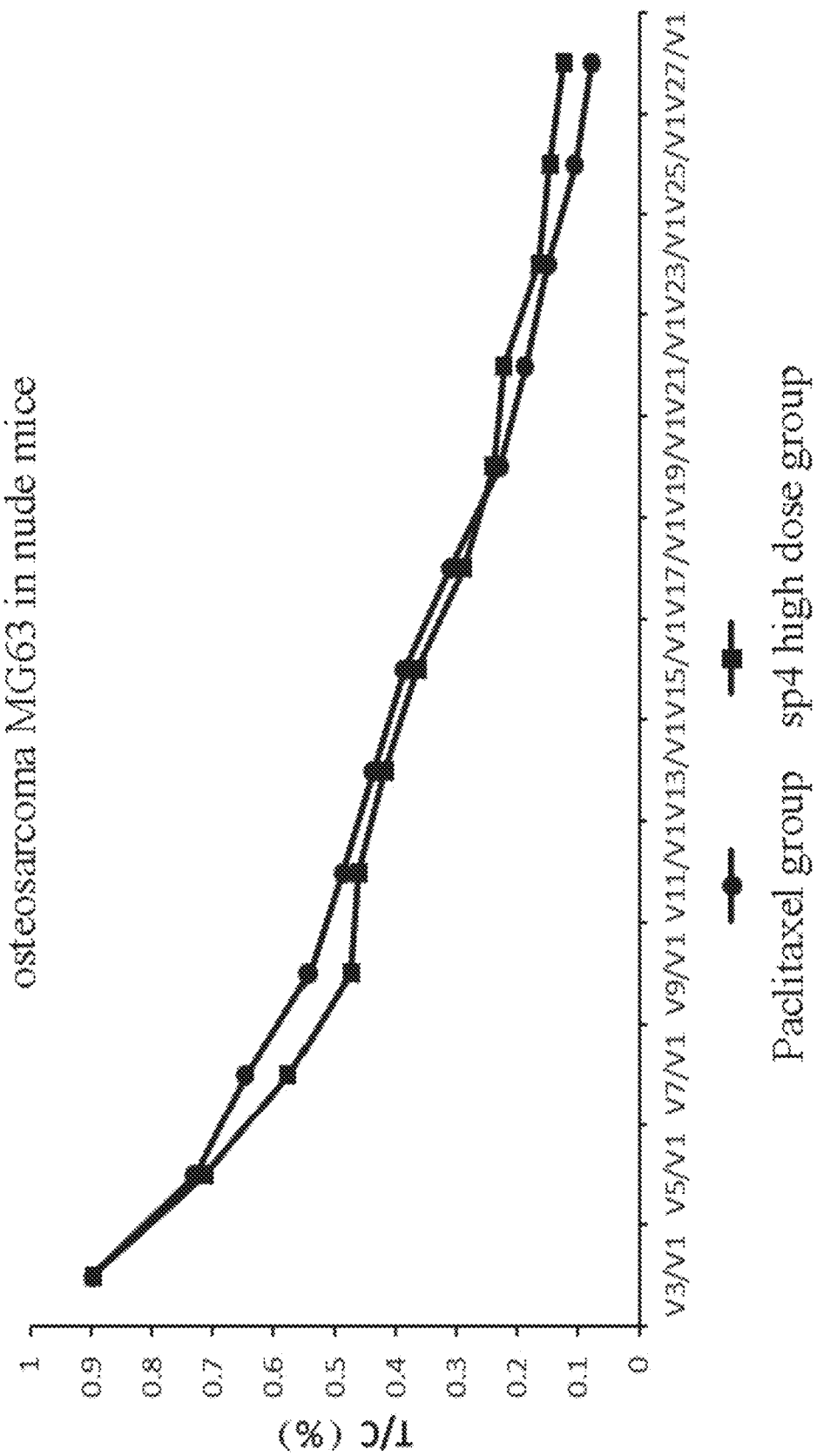
FIG. 11 illustrates in vivo anti-tumor effect evaluation index of sp4 compared with positive control Paclitaxel: relative tumor proliferation rate T/C (%). There is no significant difference between the two.

Cells with living cells ratio more than 90% were taken for experiments. Cell proliferation inhibition test adopted a cell suspension at a concentration of $1 \times 10^5$ cells/mL after cell digestion and counting, 100 μL of cell suspension ($1 \times 10^4$ cells per well) was added to each well of a 96-well plate; the 96-well plate was cultured at 37° C. in an incubator with 5% $CO_2$ for 24 hours; 100 μL of corresponding drug-containing medium was added to each well, and a negative control group, a menstruum control group, and a positive control group were established contemporaneously, with 5 wells for each group. The 96-well plates were cultured at 37° C. in an incubator with 5% $CO_2$ for 72 hours; then 10 μL of CCK-8 solution was added to each well and incubated in the incubator for 4 hours, and the OD value was read at 450 nm in a microplate reader to calculate the inhibitory rate and $IC_{50}$ values of sp4 on MG-63 and Eca-109 tumor cell lines. Evaluation criteria: the inhibition rate of different concentrations of sp4 in the same sample on the tumor cells was used for plotting to obtain a dose-effect curve (FIG. 5), and a half effective concentration ($IC_{50}$) was calculated by Logit model.

Embodiment 4

In vivo anti-tumour effect evaluation test of sp4 administered via tail veins

1. Cell Lines and Animals

Cell lines: MG-63 (human osteosarcoma cells), provided by Shanghai Meixuan Biological Science and Technology Ltd. (MXC245)

Animals: BALB/c nude mice

2. Cell Preparation Stage 2-1. the MG-63 cell lines in good resuscitation state were inoculated into a T75 cell culture flask and cultured at 37° C. with 5% $CO_2$.

2-2. the culture fluid was replaced once every 2-3 days; when the cell healing degree reached around 80% and cells passaged 3 times, there replaced about 20 times of culture fluid.

2-3. when the number of cells was subcultured enough, collected the cells after digestion and centrifugation, and adjusted the cell concentration to $5*10^7$/mL to inoculate nude mice.

3. Animal Preparation Stage 3-1. about 4-week-old BALB/c nude mice were ready to inoculate cells after one week of acclimation.

3-2. cell suspension was drawn with a 1 mL syringe (repeated shaking during this period to avoid cell sedimentation) under sterile conditions.

3-3. mice were taken out and inoculated with 100 μL of cell suspension (about $5*10^6$ cells/mouse) in a biosafety cabinet, whose inoculation sites (right forelimb armpit) were scrubbed by alcohol before inoculation; and 40 mice were inoculated.

3-4. after inoculation of cells, mice were fed with food and water as usual at 25° C. with 12 h light/darkness.

3-5. about five days after the inoculation, touched the inoculation sites to confirm whether there was a small tumor mass, and if no, cells were inoculated at double amount.

3-6. on the $8^{th}$ day after inoculation, measured the size of xenograft tumor by a vernier caliper and calculated the tumor length and width; when the tumor grew to 80-100 mm³, mice were administered in groups.

4. Administration and Handling 4-1. Nude mice were randomly divided into 5 groups: model group, positive control group, sp4 low-dose group, sp4 medium-dose group, and sp4 high-dose group, 6 mice each group (low-dose group: 4 mg/kgBW; medium-dose group: 8 mg/kgBW; high-dose group: 16 mg/kgBW; model group: injected with an equal volume of normal saline; positive control group: injected with paclitaxel at 10 mg/kgBW; administrated twice a week).

4-2. after divided into groups, animals were injected via tail veins at 4:00 pm every day; mice in the model group and the administration group were respectively injected with normal saline and drugs for 4 weeks, and the paclitaxel group was administered paclitaxel twice a week.

4-3, measured the tumor size and body weight on the day of grouping and every other day; TV=0.5*a*b², a represents long diameter, b represents short diameter.

4-4. when the experiment was finished, nude mice were sacrificed by cervical dislocation and photographed by groups; the axillary tumors were peeled off and photographed by groups, and the tumor was weighed.

4-5. depending on different requirements for the subsequent experiments, tumors were respectively stored at −80° C., 4% paraformaldehyde, and 2.5% glutaraldehyde.

4-6. according to the tumor growth data, carried on statistical analysis of tumor growth curve and relative tumor proliferation rate T/C %.

The experimental data were expressed in form of X±SD (FIGS. 6-11).

Embodiment 5

Detection of telomerase activity of MG-63 cells by sp4: Experimental methods and procedures were provided by Shanghai Meixuan Biological Science and Technology Ltd.
1. Cell Preparation
1.1 Cells Recovery
1.2 Cells Passage: After Growing Enough, the Cells were Subcultured.
1.3 Cells Plating
2. Total RNA Extraction
3. Reverse Transcription of RNA into cDNA
4. QPCR Reaction (Quantitative Polymerase Chain Reaction)

Operating procedures of Applied Biosystems 7300 was used:

1. Usually a good result was obtained with a final primer concentration of 0.2 µM.

2. ROX Reference Dye II (50×) had a lower concentration than ROX Reference Dye (50×). When using 7500 Real-Time PCR System and 7500 Fast Real-Time PCR System, the ROX Reference Dye II (50×) should be used; when using ABI PRISM 7300 Real-Time PCR System and Step One Plus™, the ROX Reference Dye (50×) should be used.

3. In a 20 µL reaction system, the added amount of DNA template is usually less than 100 ng. Because the copy number of the target genes contained in different types of DNA templates is different, gradient dilution can be performed to determine the optimal added amount of DNA template when necessary. If this product is used for the second step PCR amplification reaction of the 2-Step RT-PCR reaction, the added amount of the RT reaction solution in the first step used as a DNA template should not exceed 10% of the total volume of the PCR reaction solution.

4. The reaction solution was prepared according to the recommended system of each instrument.

Figure 12:
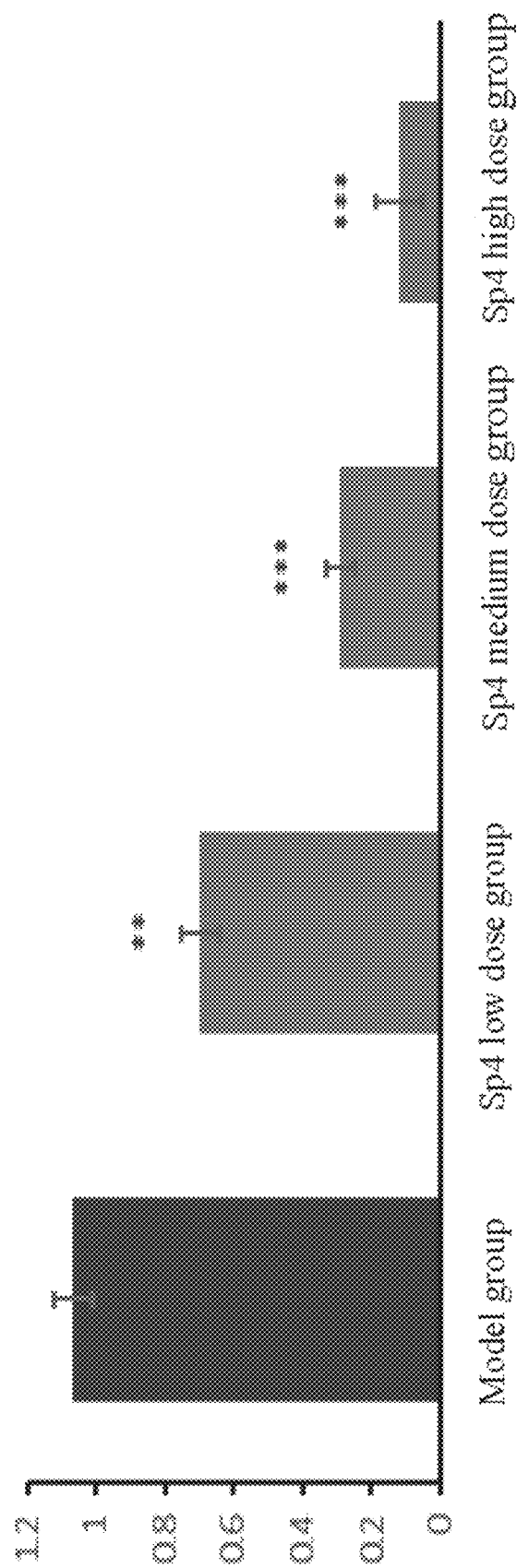
FIG. 12 illustrates a inhibitory effect of sp4 on telomerase activity of tumor cell line MG-63;  represents P<0.01; * represents P<0.001; showing a dose-dependent relationship.

5. Real Time PCR was performed according to 2-step PCR standard procedure. (FIG. 12)

Embodiment 6

Detection of Telomerase Activity in Solid Tumors
1. Sample preparation: Tumor samples taken at the end of anti-tumor effect experiments in nude mice
2. Extraction of total RNA
3. Reverse transcription of RNA into cDNA
4. QPCR reaction: operating procedures of Applied Biosystems 7500 was used 1) Preparation of PCT reaction solution
Good results were usually obtained with a final primer concentration of 0.2 µM. The primer concentration could be adjusted within a range of 0.1 to 1.0 µM.

2) ROX Reference Dye II (50×) had a lower concentration than ROX Reference Dye (50×). When using 7500 Real-Time PCR System and 7500 Fast Real-Time PCR System, the ROX Reference Dye II (50×) should be used; when using ABI PRISM 7300 Real-Time PCR System and Step One Plus™, the ROX Reference Dye (50×) should be used.

3) In a 20 µL reaction system, the added amount of DNA template is usually less than 100 ng. Because the copy number of the target genes contained in different types of DNA templates is different, gradient dilution can be performed to determine the optimal added amount of DNA template when necessary.

4) The reaction solution was prepared according to the recommended system of each instrument.

5) Real Time PCR was performed according to 2-step PCR standard procedure.

Figure 13:
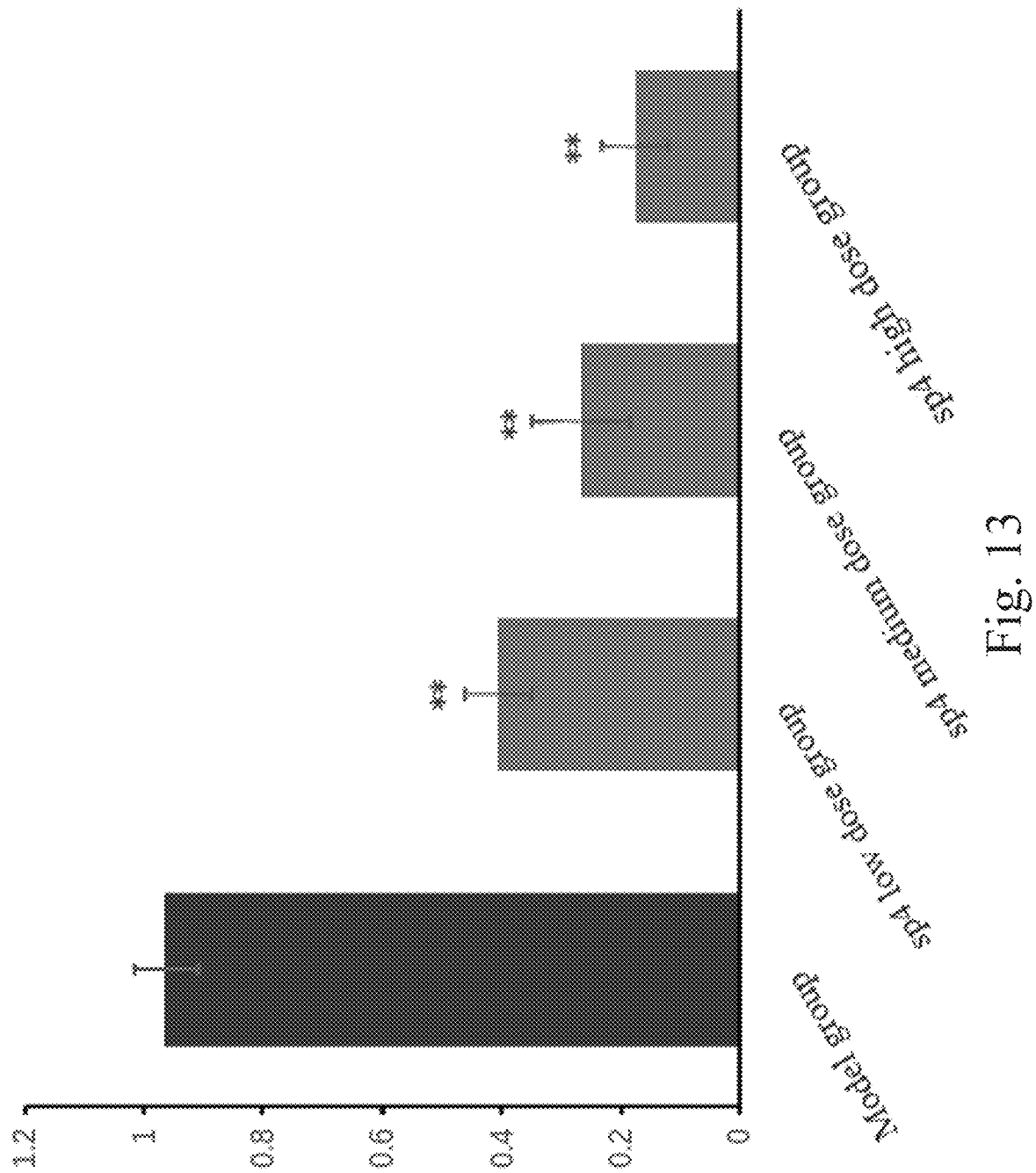
FIG. 13 illustrates a inhibitory effect of sp4 on telomerase activity of human osteosarcoma MG-63 in vivo tumor tissues in nude mice; ** represents the administration group has significant difference (P<0.01) in telomerase activity changes compared with that of in the MG-63 cell subcutaneous tumor model group, showing a dose-dependent relationship.
Figure 14A:
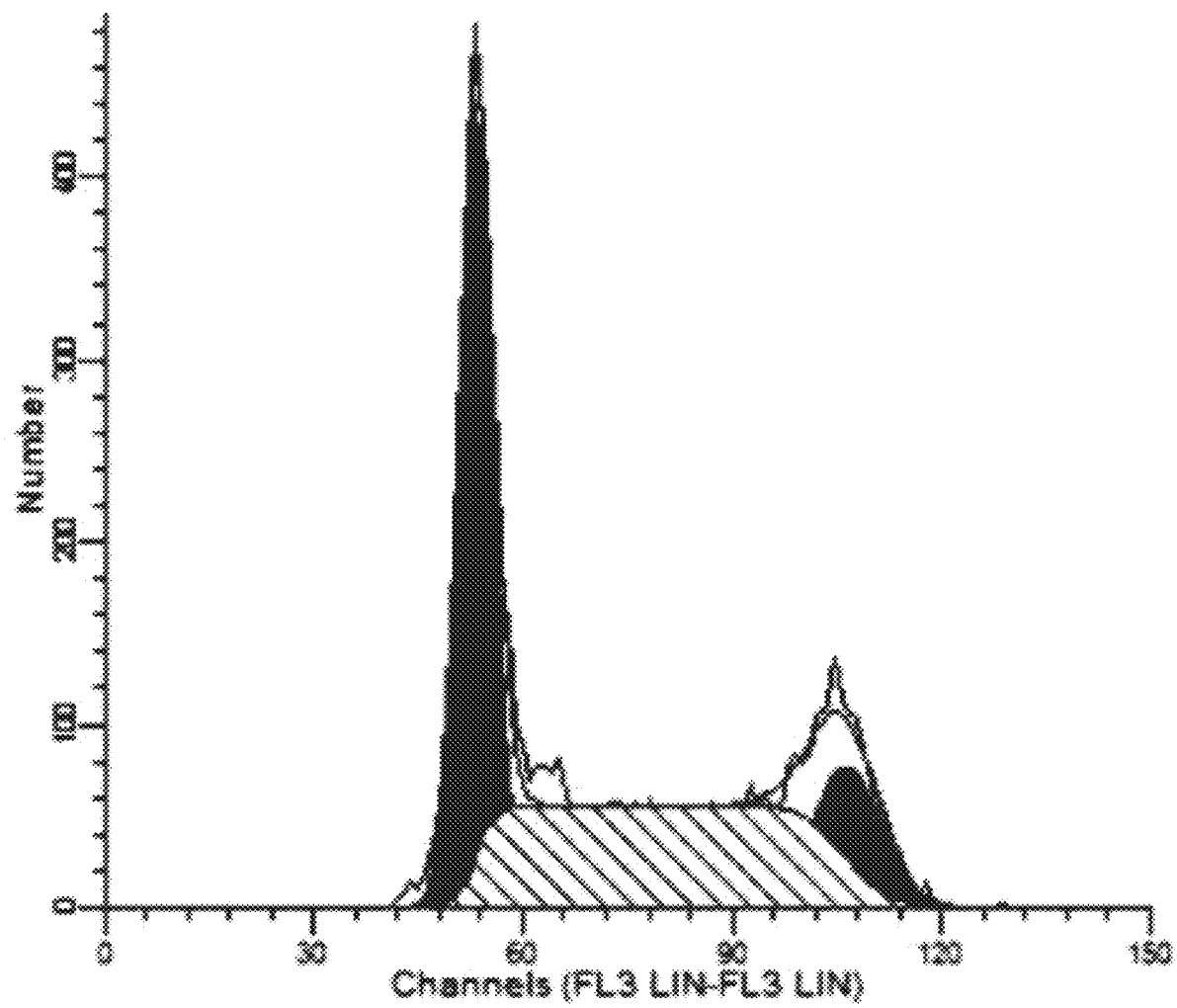
FIGS. 14A-E illustrate sp4 involves in regulation of HL-60 tumor cell cycle: the effects of different doses of sp4 on the HL-60 cell cycle.
Figure 14B:
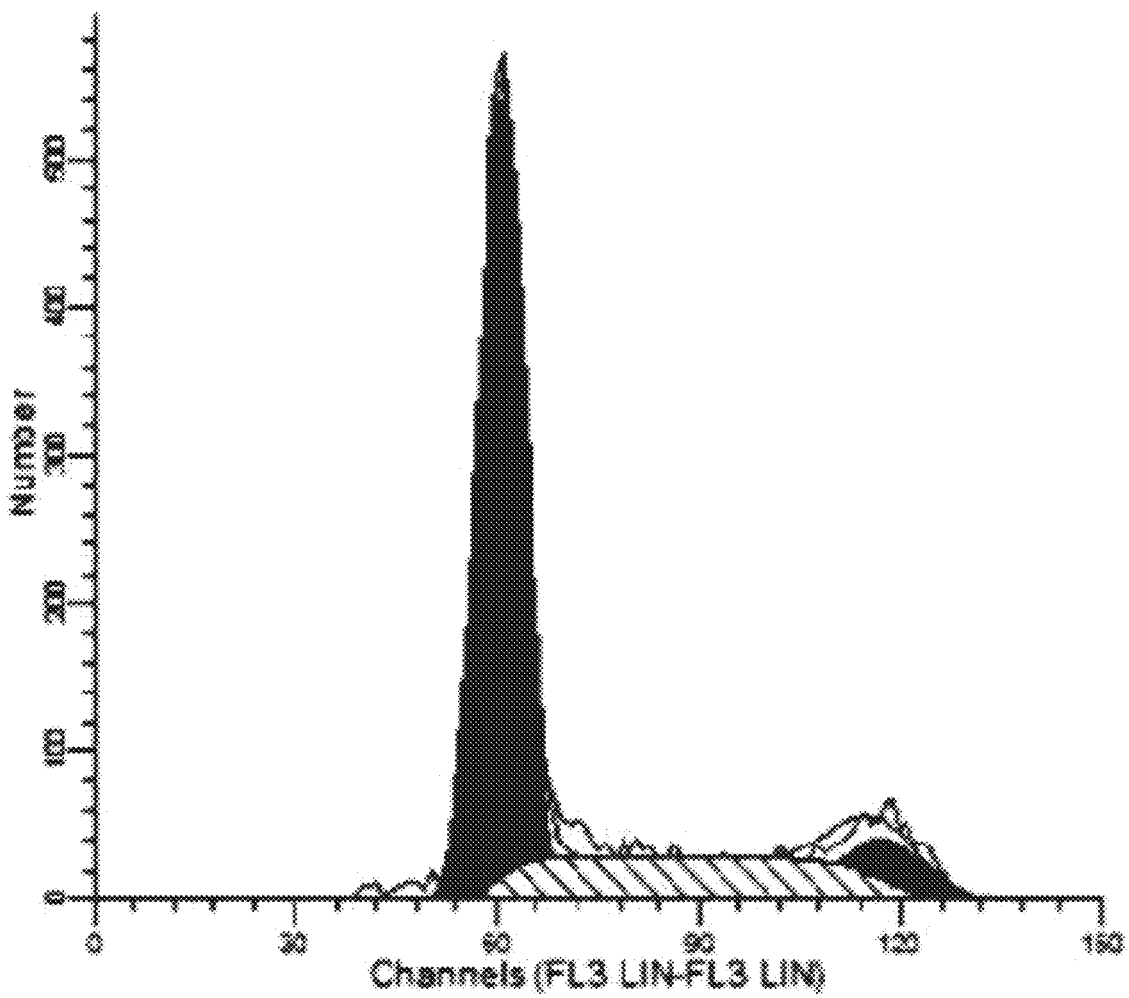
Figure 14C:
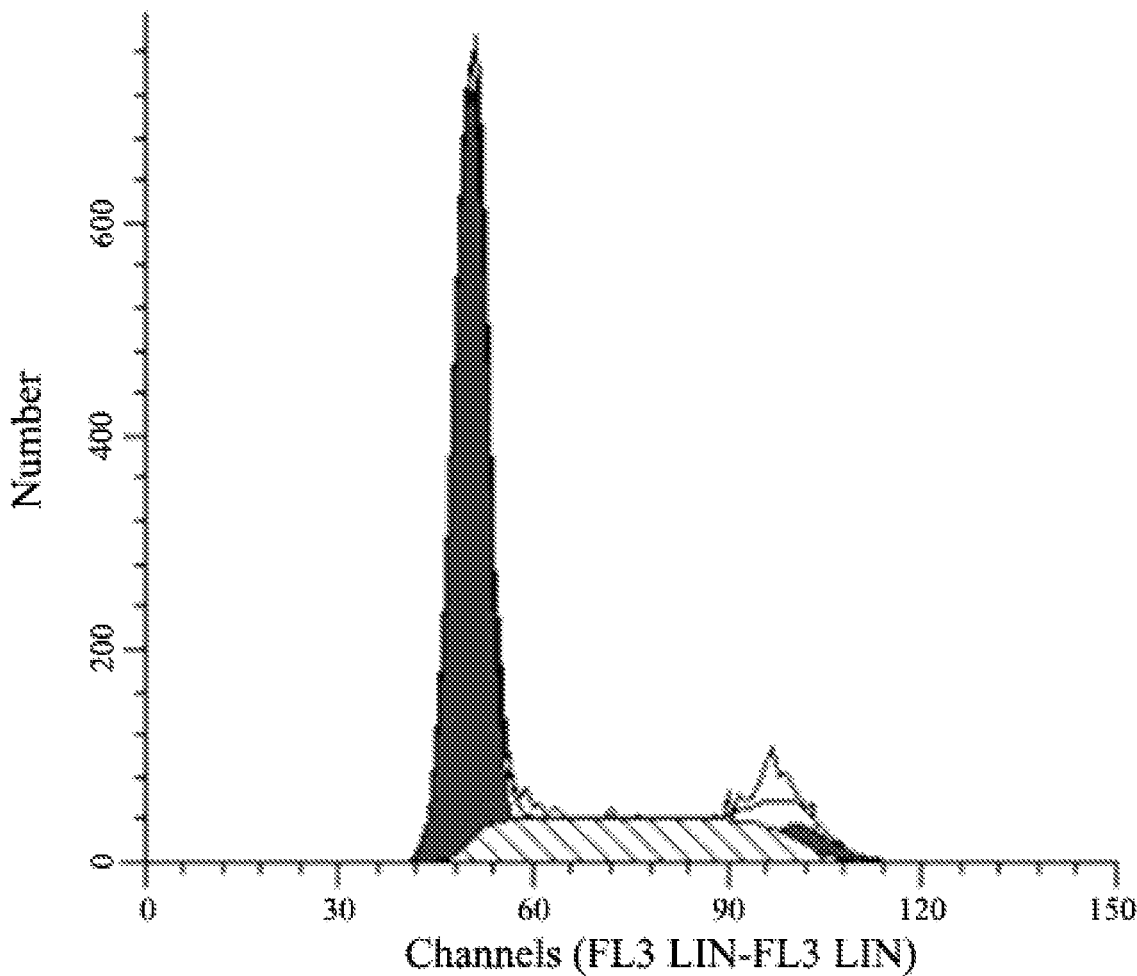
Figure 14D:
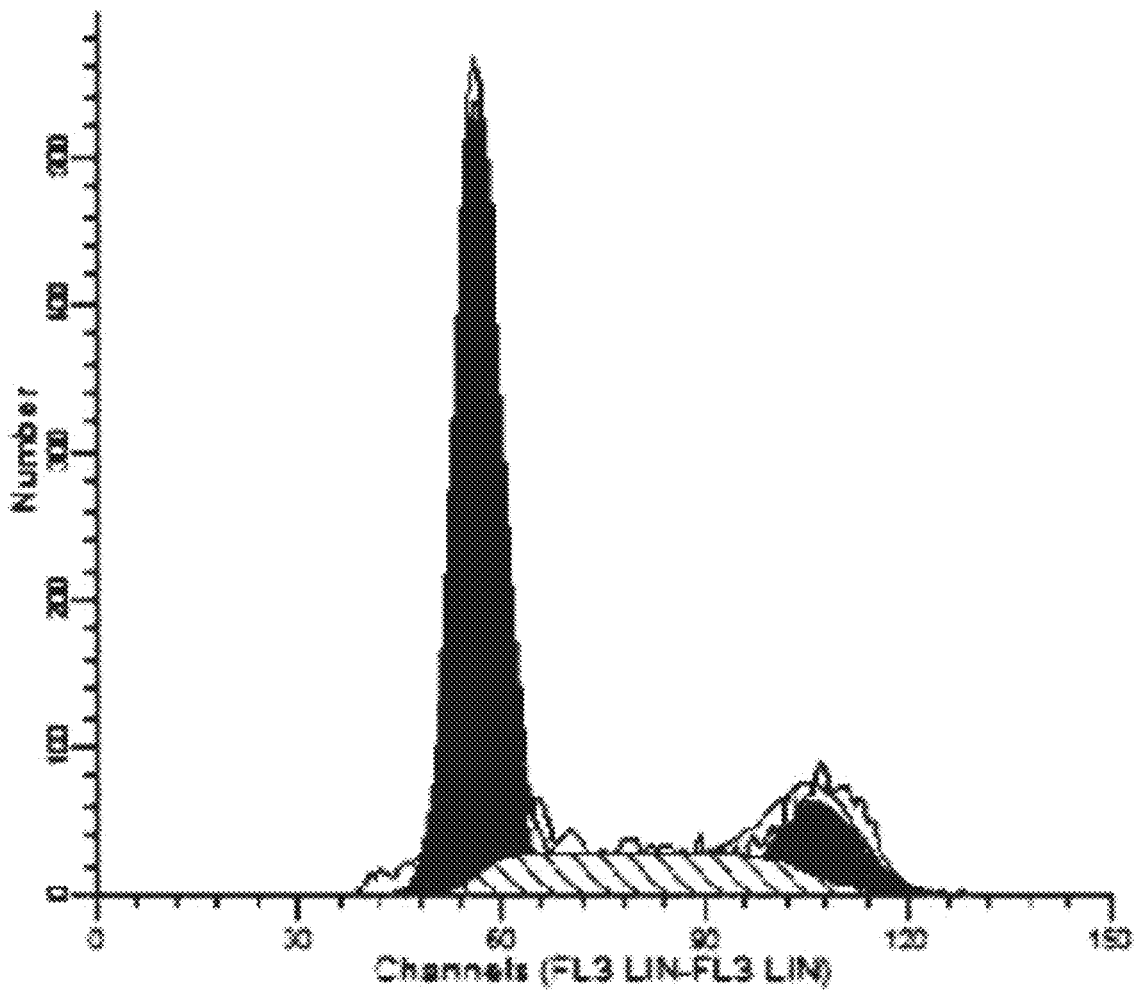
Figure 14E:
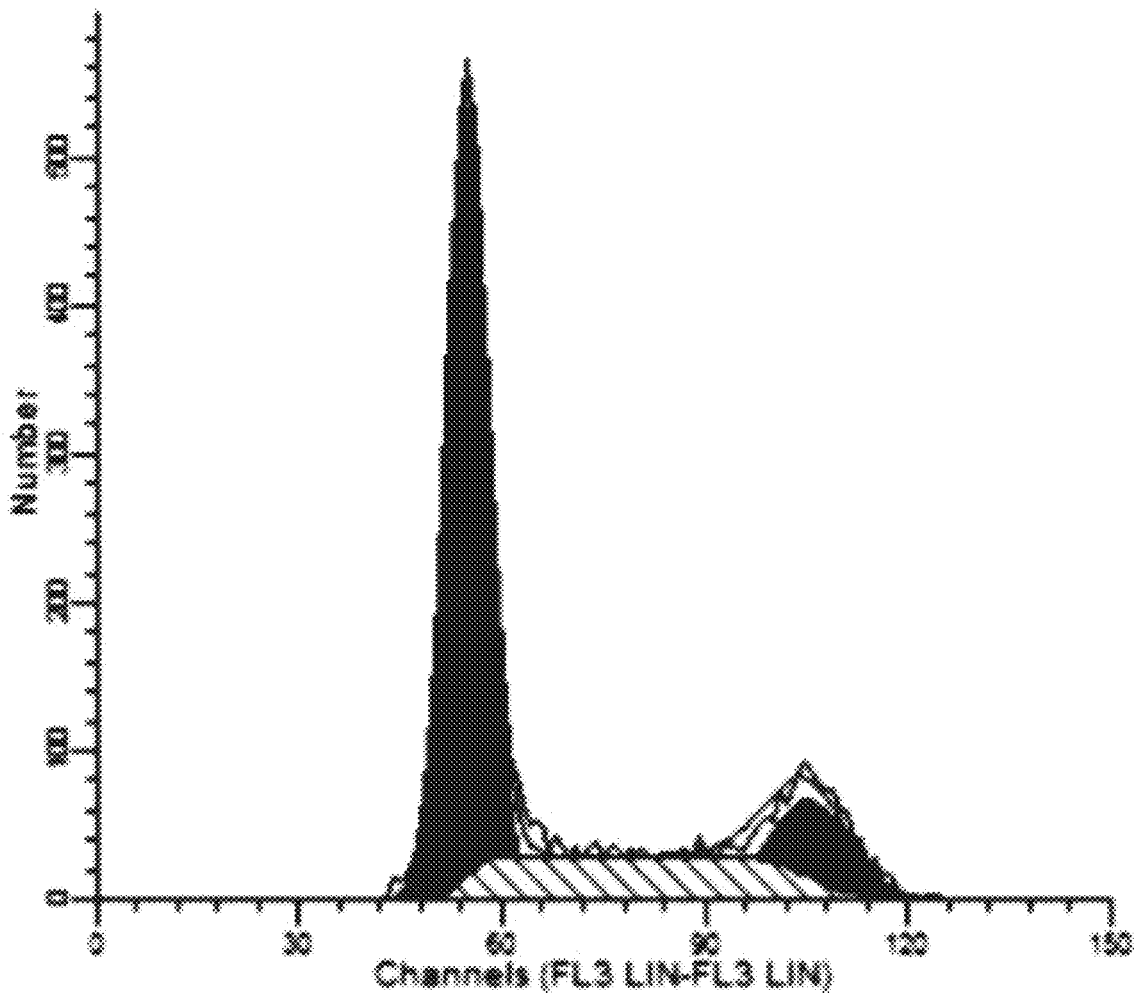

6) Analysis of experimental results. (FIG. 13)

Embodiment 7 Detection of Cell Cycle (A) Detection of HL-60 Cell Cycle:
Propidium iodide (PI for short) is a fluorescent dye for double-stranded DNA. The combination of propidium iodide and double-stranded DNA can generate fluorescence, and the intensity of fluorescence is proportional to the content of double-stranded DNA. After DNA in the cell being stained by propidium iodide, DNA content in cells was determined by flow cytometry, and then cell cycle analysis was performed based on the distribution of DNA content.

1. Cells culture were performed
2. The cultured cells were performed trypsinization with 0.25% trypsin in different groups to make them into single cell, then cell suspension was mixed well and collected into flow cytometric tubes;
3. Taken 1000 g cell suspension to be centrifuged for 5 min, the supernate was removed and the precipitate was suspended with 3004, PBS solution containing 10% fetal bovine serum, and transferred to a clean 1.5 mL centrifuge tube;
4. The centrifuge tube was added with 7004, of absolute ethanol and placed at −20° C. to immobilize cells for more than 24 hours;
5. The immobilized cells were centrifuged at 3,000 g for 30 sec, and then the supernatant was removed;
6. The cell precipitation was suspended with 1004, of 1 mg/mL RNase A solution, and the RNA in the cells was digested at 37° C. in a incubator;
7. The digestion product was added with 400 µL of 50 µg/mL Propidium Iodide (PI) solution, and nuclei were stained for 10 min in the dark. Cell DNA content was determined by flow cytometry, to determine the proportion of cells in each cell cycle.

TABLE 1

Cell cycle of human promyelocytic leukemia cell line HL-60 detected by flow cytometry at different concentrations of sp4 (%)

| Sample | DipG1 (%) | DipG2 (%) | DipS (%) | G2/G1 | % CV | Total S-Phase (%) |
|---|---|---|---|---|---|---|
| NC (HL-60 ONLY) | 41.43 | 14.29 | 44.29 | 2.00 | 4.70 | 44.29 |
| sp4 (200 µM) | 66.54 | 9.69 | 23.76 | 1.93 | 5.33 | 23.76 |
| sp4 (100 µM) | 65.79 | 6.03 | 28.17 | 2.00 | 5.18 | 28.17 |

TABLE 1-continued

Cell cycle of human promyelocytic leukemia cell line HL-60 detected by flow cytometry at different concentrations of sp4 (%)

| Sample | DipG1 (%) | DipG2 (%) | DipS (%) | G2/G1 | % CV | Total S-Phase (%) |
|---|---|---|---|---|---|---|
| sp4 (50 μM) | 64.76 | 14.23 | 21.01 | 1.89 | 5.89 | 21.01 |
| sp4 (25 μM) | 62.32 | 14.85 | 22.82 | 1.92 | 5.70 | 22.82 |

Compared with the control group, after adding sp4, the expression of HL-60 cells in the G0/G1 phase was increased significantly, the expression of cells in the G2/M phase and S phase was decreased, presenting G1 phase arrest; in addition, with the increased dose of sp4, the proportion of cells in G1 phase was increased accordingly. It suggests that sp4 could prevent human promyelocytic leukemia cell line HL-60 cells from transitioning from G1 phase to S phase, cause G1 phase arrest in the cell cycle, reduce mitosis and thereby inhibit cell proliferation; and, with the increase of sp4 dose, the effect is better (FIG. 14A-E).

(B) Detection of Human Osteosarcoma MG-63 Cell Cycle in Nude Mice

1. Preparation of Single Cell Suspension of Solid Tumor 1.1 Tumor block was washed 3 times with PBS buffer and cut into small blocks (1-2 mm), then washed 3 times with PBS, and transferred into a 50 ml centrifuge tube.

1.2 0.25% trypsin solution was added to digested at 37'C for 20-40 min, and gently shaken once every 5 min, to separate cells. 1.3 2 to 5 ml of serum-containing medium was added to terminate the trypsin digestion.

1.4 The suspension was stood for 2-3 min, and transferred to a new centrifuge tube, and filtered with a 200-mesh nylon mesh twice.

1.5 The filtered suspension was centrifuged at 1000 rpm for 5 min, and removed the supernatant.

1.6 5 ml of PBS buffer was added to centrifuge again, and removed the supernatant.

1.7 1 to 2 ml of culture solution was added according to the amount of cells, and the cells were counted for standby.

2. Detection of Cell Cycle

1) The cell culture solution was collected into a centrifuge tube for standby. Cells were digested with trypsin until the cells could be gently blown down with a pipette or pipette tip, then the collected cell culture solution was added and centrifuged at about 1000 g for 3-5 minutes to precipitate cells. The supernatant was removed, and 1 ml of ice-bath pre-chilled PBS was added to re-suspend the cells and transferred to a 1.5 ml centrifuge tube. The cells were centrifuged and precipitated again, the supernatant was removed, the bottom of the centrifuge tube was gently stricken to disperse cells properly.

2) Cell fixation: 1 ml of ice-bath pre-cooled 70% ethanol was added to gently blow and mix well, and fixed at 4° C. for 2 hours, centrifuged at 1000 g for 3-5 minutes to were precipitate the cells. The supernatant was removed and approximately 1 ml of ice-bath pre-cooled PBS was added to resuspend the cells. The cells were centrifuged and precipitated again, and the bottom of the centrifuge tube was gently stricken to disperse cells properly.

3) Preparation of propidium iodide staining solution: appropriate amount of propidium iodide staining solution was prepared according to the number of samples to be tested. Note: The prepared propidium iodide staining solution could be stored at 4° C. for a short period of time and should be used on the same day.

4) Staining: 0.5 ml of propidium iodide staining solution was added to each tube of cell samples, slowly and fully resuspended the cell precipitate and incubated at 37° C. in the dark for 30 minutes, and subsequently stored at 4° C. or in an ice bath protected from light. After staining, flow cytometry should be completed within 24 hours.

5) Flow cytometry detection and analysis: the red fluorescence was detected by a flow cytometer at the excitation wavelength of 488 nm, and the light scattering was detected also. Cell DNA content and light scattering analyses were carried out by analysis software.

Figure 15:
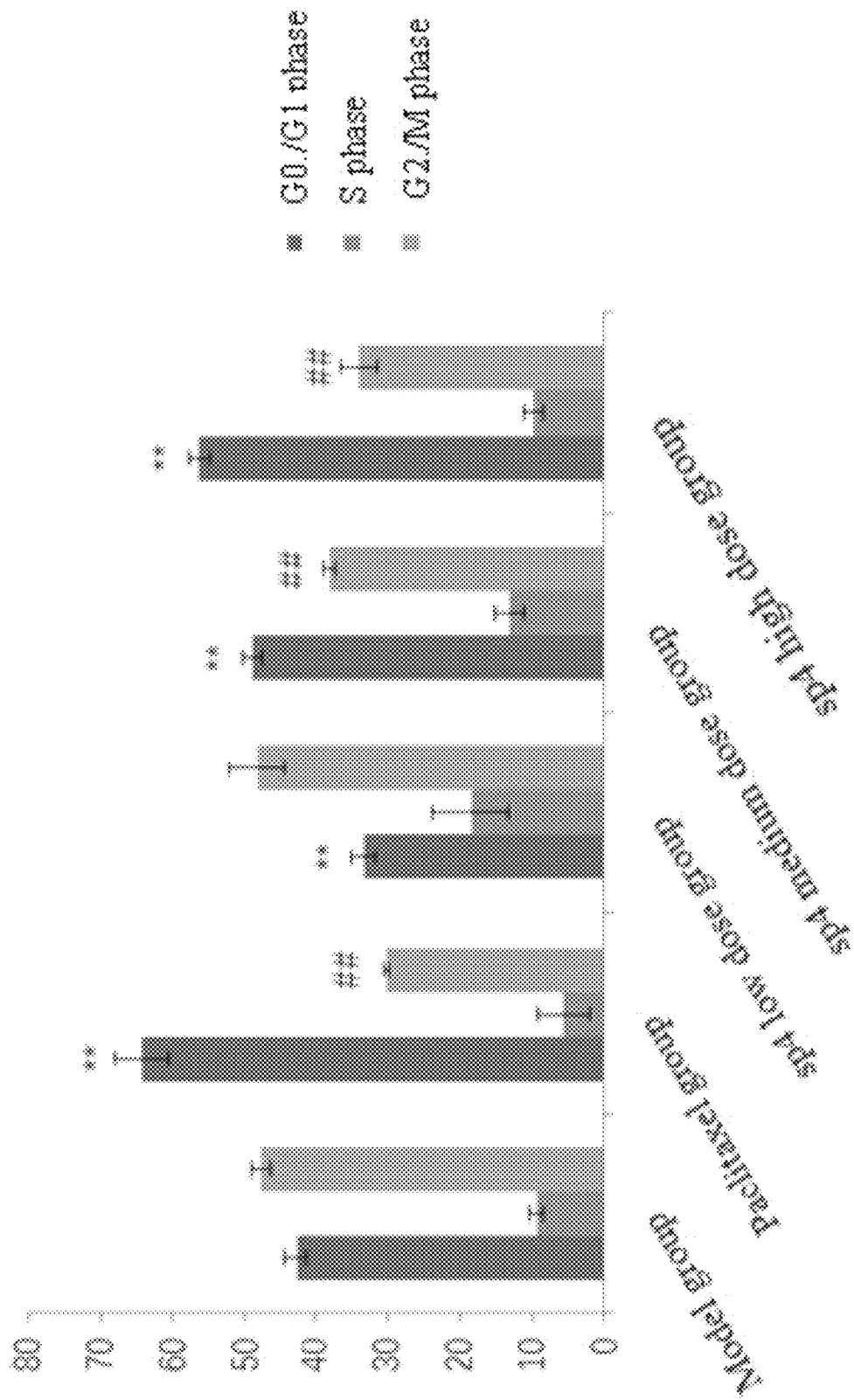
FIG. 15 illustrates changes of subcutaneous human osteosarcoma cell cycle in nude mice with administration of sp4; in the figure, ** represents that there is a significant difference in G0/G1 phase between each group and the model group; ## represents that there is a significant difference in G2/M phase between each group and the model group.

Results: Compared with the model group, the G0/G1 phase increases significantly (P<0.01), and the S and G2/M phases decreases in the sp4 moderate dose group; in the sp4 high-dose group, the G0/G1 phase increases significantly (P<0.01), and the S and G2/M phases decreases. and the G2/M phase decreases significantly (P<0.01); and in the sp4 low-dose group, the G0/G1 phase decreases significantly (P<0.01), and the S and G2/M phases increases, showing a dose-response relationship. (FIG. 15)

Embodiment 8 Animal Acute Toxicity Test—Maximal Tolerable Dose (MTD)

I. Experimental Conditions: GLP

1. Test animal: Healthy adult ICR mice, male, weight 19-20 g, n=10;

2. Test sample: sp4;

3. Test sample preparation method;

4. Administration route: tail vein injection in mice;

5. Dosing volume: 0.5 ml/time;

6. Frequency of administration: in accordance with FDA guidelines;

Acute toxicity refers to the toxic reaction produced by a drug within a certain period of time after a single dose or multiple-dose within 24 hours. In narrow sense, a single dose toxicity study is to investigate the acute toxic reactions after a single administration of a test substance. This guideline refers to single dose toxicity study in a broad sense, which can be obtained by single or multiple dosing within 24 hours;

II. Detection of Maximal Tolerable Dose (MTD)

MTD refers to the highest dose that does not cause deaths of test animals. Firstly, the working solutions at three concentrations that would not cause the death of test animals were prepared, and one animal was injected via tail veins (1.5 mL, by 3 times). The first dose was 1.5 mL of working solution with 1150 mg/kgBW, which was injected to mice by 3 times via tail veins within 24 hours. On the next day, if no death was found, the remaining 9 animals were injected with the same dose via tail veins (a total of n=10); if the first animal died, the dose would be reduced. Performed in turn and the results show that, when the dose was 700 mg/kgBW and mice were administered by three times within 24 h, no toxic reactions and deaths occurred (shown in Table 2). ICR mice were injected with a sp4 working solution at a dose of 700 mg/kgBW, and continued to be observed, no toxic reactions and deaths occurred within 2 weeks after administration (shown in Table 3).

TABLE 2

MTD test of the 700 mg/kg · BW dose group

| Animal No. | Body Weight (g) | Dose (mg/kg) | Time of Administration | Toxic Signs | Survival or not | Survival Rate % |
|---|---|---|---|---|---|---|
| 1 | 20.5 | 700 | 3 times/9 h | Reduced activity of mice | Survival | 100 |
| 2 | 20.6 | 700 | 3 times/9 h | Reduced activity of mice | Survival | |
| 3 | 20.7 | 700 | 3 times/9 h | Reduced activity of mice | Survival | |
| 4 | 20.4 | 700 | 3 times/9 h | None | Survival | |
| 5 | 20.2 | 700 | 3 times/9 h | No abnormal behavior observed | Survival | |
| 6 | 20.9 | 700 | 3 times/9 h | No abnormal behavior observed | Survival | |
| 7 | 20.1 | 700 | 3 times/9 h | Reduced activity of mice | Survival | |
| 8 | 20 | 700 | 3 times/9 h | No abnormal behavior observed | Survival | |
| 9 | 20.3 | 700 | 3 times/9 h | No abnormal behavior observed | Survival | |
| 10 | 20.2 | 700 | 3 times/9 h | Reduced activity of mice | Survival | |

TABLE 3

Mice weight of 700 mg/kg · BW dose group

| Date | No. 1 | No. 2 | No. 3 | No. 4 | No. 5 | No. 6 | No. 7 | No. 8 | No. 9 | No. 10 |
|---|---|---|---|---|---|---|---|---|---|---|
| 2018 May 15 | 20.5 | 20.6 | 20.7 | 20.4 | 20.2 | 20.9 | 20.1 | 20 | 20.3 | 20.2 |
| 2018 May 16 | 20.5 | 21.3 | 21.2 | 20.8 | 20.4 | 21.5 | 20.4 | 20.5 | 20.5 | 20.7 |
| 2018 May 17 | 21.1 | 21.7 | 21.3 | 21.4 | 20.8 | 22.2 | 21.2 | 20.8 | 21.1 | 21.1 |
| 2018 May 18 | 21.5 | 22.1 | 21.9 | 21.7 | 21.5 | 22.7 | 21.9 | 21.1 | 21.9 | 21.5 |
| 2018 May 19 | 21.9 | 22.6 | 22.6 | 22.5 | 21.8 | 23 | 22.5 | 21.8 | 22.5 | 21.6 |
| 2018 May 20 | 22.3 | 22.8 | 22.8 | 22.8 | 22.4 | 23.7 | 22.9 | 22.5 | 22.8 | 22.8 |
| 2018 May 21 | 22.7 | 23.5 | 23.1 | 23.1 | 22.9 | 24.1 | 23.3 | 23.1 | 23.4 | 22.9 |
| 2018 May 22 | 23.3 | 24.1 | 23.5 | 23.6 | 23.2 | 24.8 | 23.8 | 23.4 | 23.8 | 23.5 |
| 2018 May 23 | 24.0 | 24.8 | 24.2 | 24.2 | 23.7 | 25.1 | 24.5 | 24.4 | 24.1 | 24.1 |
| 2018 May 24 | 24.7 | 25.2 | 24.7 | 24.7 | 23.9 | 25.6 | 25.1 | 24.8 | 24.6 | 24.7 |
| 2018 May 25 | 25.3 | 25.8 | 25.1 | 25.1 | 24.8 | 26.1 | 25.5 | 25.1 | 24.9 | 25.5 |
| 2018 May 26 | 25.8 | 26.3 | 25.9 | 25.6 | 25.2 | 26.5 | 25.9 | 25.5 | 25.6 | 25.9 |
| 2018 May 27 | 26.1 | 26.8 | 26.3 | 26.2 | 26.4 | 27.2 | 26.3 | 26 | 25.8 | 26.2 |
| 2018 May 28 | 27.2 | 27.3 | 26.9 | 26.8 | 26.8 | 27.7 | 26.8 | 26.4 | 26.6 | 27.1 |
| 2018 May 29 | 28.1 | 28.5 | 27.2 | 27.6 | 27.5 | 28.3 | 27.5 | 27.1 | 27.1 | 27.9 |

Figure 16:
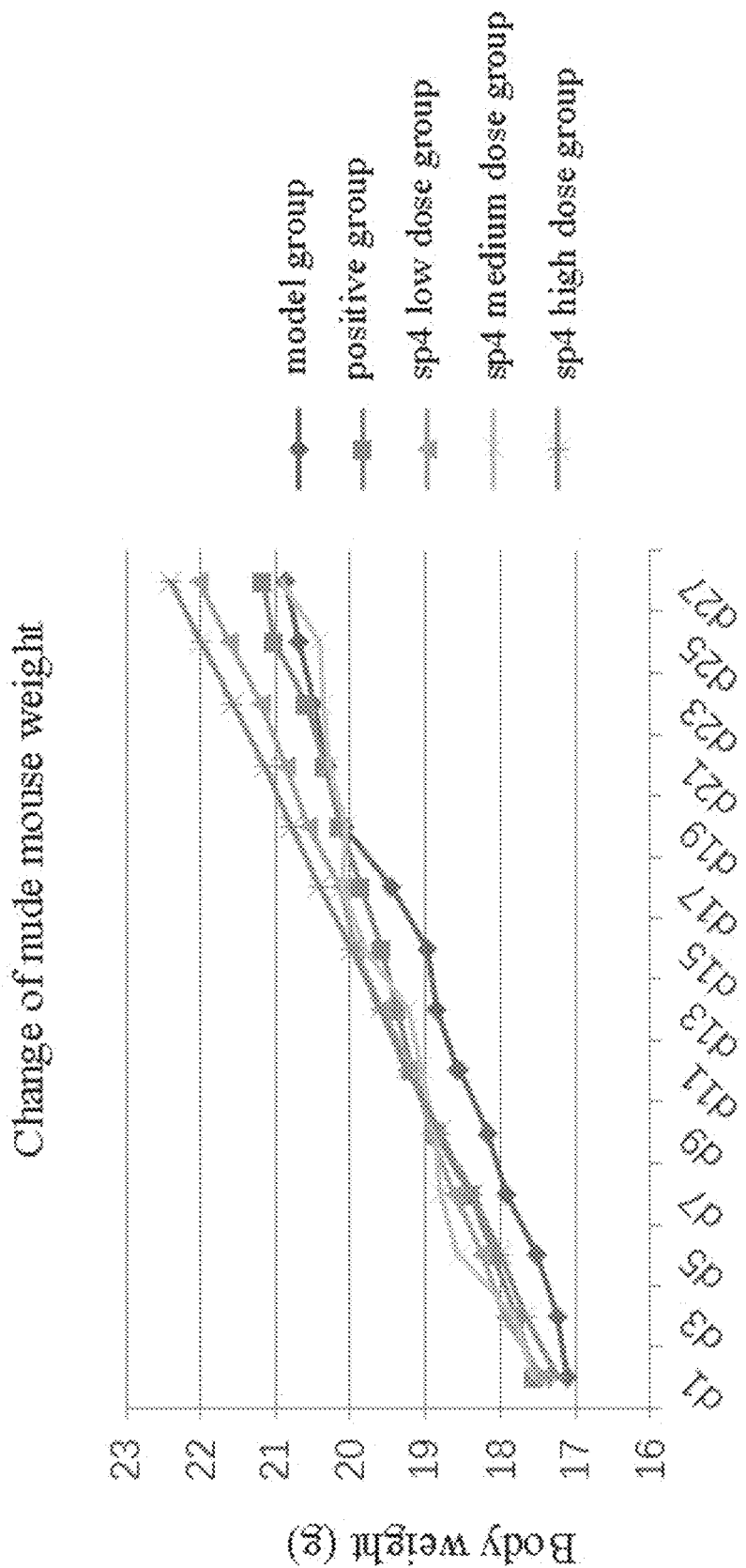
FIG. 16 illustrates changes in body weight of tumor-bearing nude mice in each group in 4 weeks with intravenous administration of sp4.

In addition, in the in vivo efficacy test, the weight gain in each treatment group was not significantly different from that of the control group (P>0.05), and no death occurred, as shown in FIG. 16.

Embodiment 9

Immunofluorescence Test of Sp4 on PD-L1 and CD47
Samples: Subcutaneous human osteosarcoma MG-63 xenograft tumor tissues in nude mice
2. Antibody:

| Antibody | Source | Manufacturer | Cargo No. |
|---|---|---|---|
| PD-L1 | Rabbit | Abcam | Ab213480 |
| CD47 | Rabbit | proteintech | 18470-1-AP |

3. Experimental steps:
3-1. Tissue sections
3-2. Tissue dewaxing and hydration
3-3. Antigen retrieval
The tissue sections were placed in a container containing citrate buffer (0.01 mol/L, pH6.0), and heated in a microwave oven to maintain the liquid in the container at about 98° C. for 10-15 min. The container was taken out and cooled at room temperature for 20-30 min, and the sections were washed with PBS (0.01M, pH 7.4) for 3 times, 5 min each time. The sections were repaired in hot steam of antigen retrieval buffer for 20 min and naturally cooled to room temperature.

3-4. The PBS was removed and 5% BSA/0.01 MPBS was used for blocking for 30 min, without washing and 5% BSA blocking solution was absorbed by absorbent paper from the edges. The diluted antibody solution (diluent was 5% BSA prepared with PBS) was added dropwise. In the blank control group, PBS (0.01M, pH=7.4) was used to replace the antibody and incubated in a wet box at 4° C. refrigerator overnight.

3-5. The next day, the wet box was taken out from the refrigerator, and placed at room temperature for 15 minutes. PBS (0.01M, pH=7.4) was used to wash the blank control group 5 times and 5 min each time. The surplus PBS was absorbed, and fluorescent secondary antibody was added dropwise, and incubated at room temperature for 30 minutes in the dark; washed 5 times with PBS and 5 min each time.

3-6. DAPI was added dropwise to incubate for 2 minutes in the dark, and nucleation and blue fluorescence occurred. DAPI was removed with PBS for 1 min×3 times.

3-7. Finally, the sections were blocked with glycerol and observed immediately under a fluorescence microscope.

4. Analysis Method:

The data provided were average optical density (IOD, abbreviated as OD) and positive area ratio (positive area/total area.) The results were analyzed by using positive index.

Positive index=Positive area ratio×OD

Figure 17:
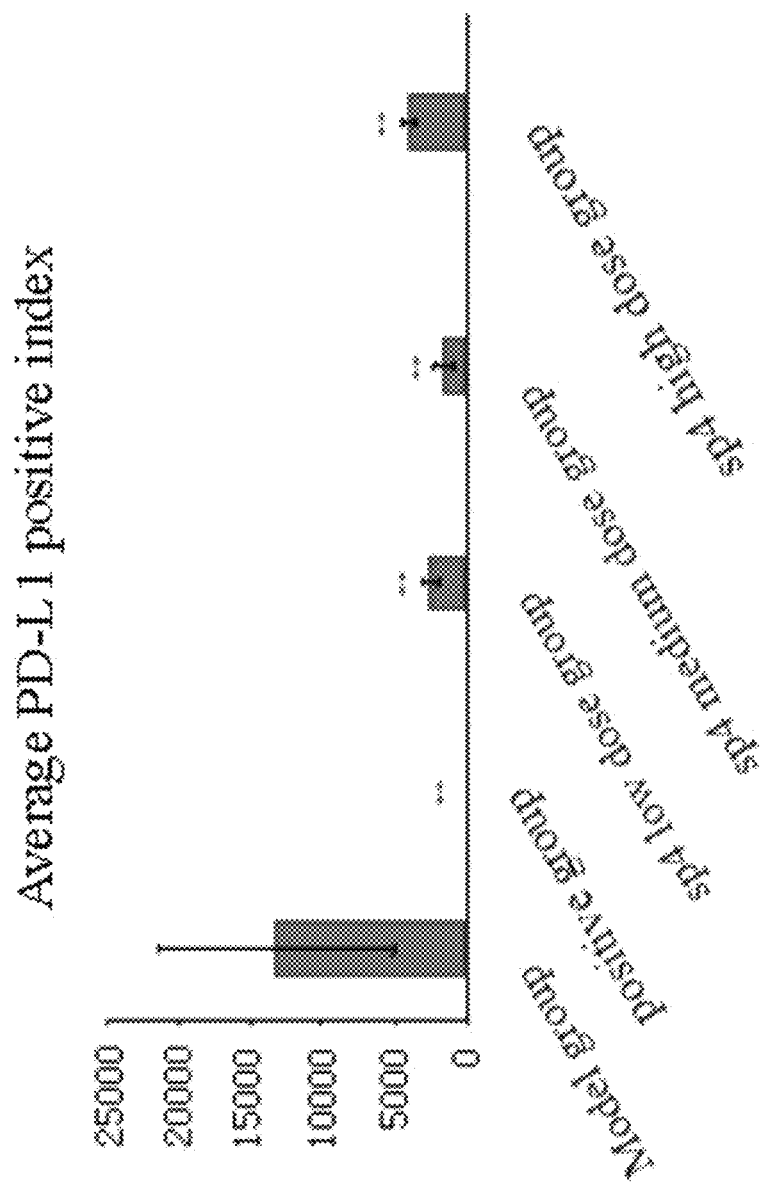
FIG. 17 illustrates that sp4 significantly inhibits the high expression of PD-L1 in tumor cells; * represents that there is a difference (P<0.05) compared with the model group; ** represents that there is a significant difference (P<0.01) compared with the model group.
Figure 18:
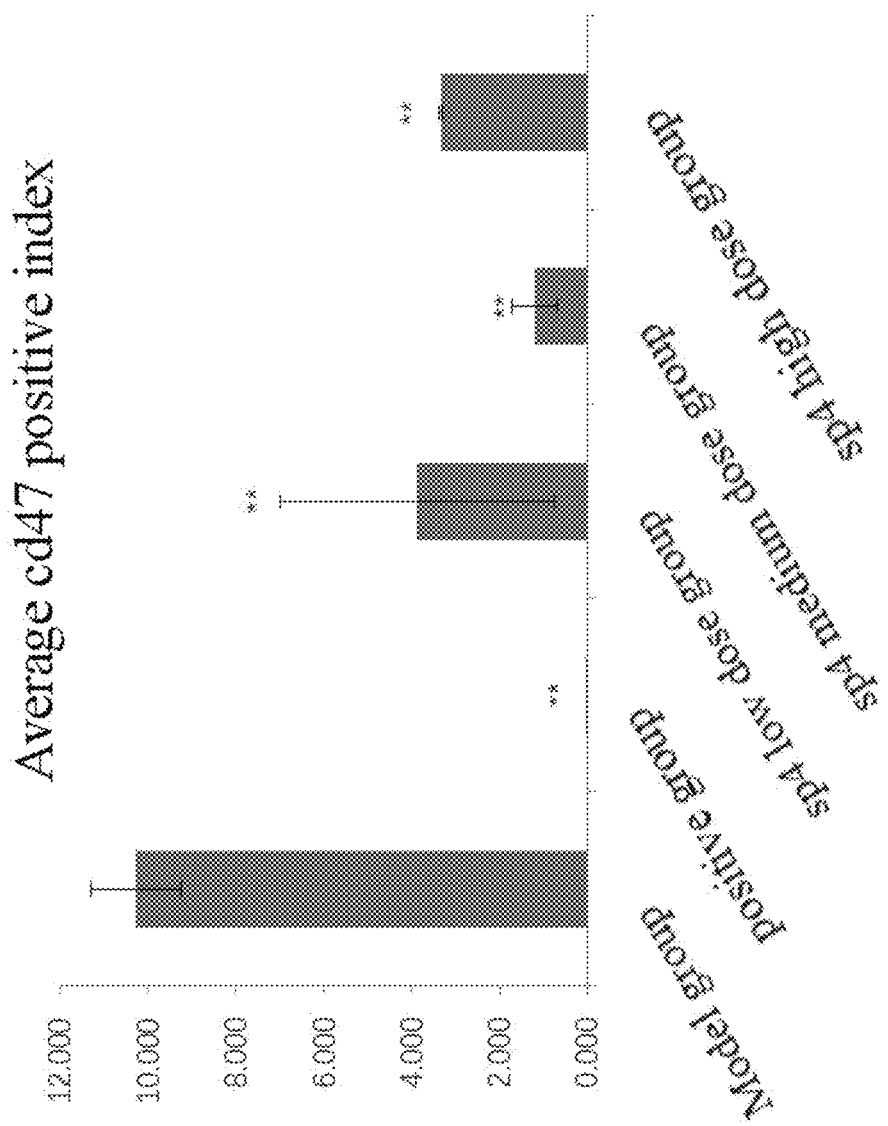
FIG. 18 illustrates that sp4 significantly inhibits the high expression of CD47 in tumor cells; * represents that there is a difference (P<0.05) compared with the model group; ** represents that there is a significant difference (P<0.01) compared with the model group.

Results: Compared with the model group, the expression of CD47 in the sp4 administration group was significantly reduced; the expression of PD-L1 was significantly decreased in the sp4 group compared with the model group. It shows that sp4 can significantly inhibit the high expression of CD47 and PD-L1 in tumor cells. The CD47 on the surface of tumor cells interacted with SIRPa on the surface of macrophages to send out immunosuppressive signals, thereby protecting tumor cells from phagocytosis by macrophages. The PD-L1 on the surface of tumor cells bound to PD-1 molecules on immune cells to inhibit the T cell activity. Therefore, sp4 can significantly inhibit the high expression of CD47 and PD-L1 in tumor cells, and enhance the immunity to clear tumor cells and restore the ability of macrophages and T cells to recognize tumor cells (FIGS. 17, 18).

Embodiment 10

Induced Differentiation Experiment:

1. HE Staining Method (Suspension Cells)
1) Smear and Fixation
2) Staining

Staining by Hematoxylin, Eosin, and Blocking with Neutral Gum

3) Results and Analysis of HE Staining (Suspension Cells)

(20) Photograph under oil lens of microscope, and collection and analysis by Lecia Applaction Stiue image system.

TABLE 4

SP4 on mature, immature HL-60 (human acute myeloid leukemia) cells (%)

| No. | Mature cells (%) | Immature cells (%) |
|---|---|---|
| C (control) | 40.1 | 59.9 |
| SP4 200 μM | 58.6 | 41.4 |

TABLE 4-continued

SP4 on mature, immature HL-60 (human acute myeloid leukemia) cells (%)

| No. | Mature cells (%) | Immature cells (%) |
|---|---|---|
| SP4 100 μM | 57.0 | 43.0 |
| SP4 50 μM | 46.3 | 53.7 |
| SP4 25 μM | 43.3 | 56.7 |

2. Nitroblue Tetrazolium (NBT) Reduction Reaction

1) Principle: Nitrotetrazolium (NBT) is a water-soluble light yellow reactive dye. When it is reduced by neutrophil enzymes, it becomes water-insoluble blue-black formazan particles and precipitates in the cytoplasm.

2) Method

① Cell Culture:

Cell: HL-60 cell line, was cultured in RPM11640 medium containing 15% fetal bovine serum at 37° C. with 5% $CO_2$ saturated humidity condition. Cells in the logarithmic growth phase were used for experiments.

② Preparation of Synthetic Peptide Stock Solution:

3000 μg of sp4 lyophilized powder was completely dissolved in 1.20 ml of ultrapure water (the concentration is 2000 μM, that is, 2502 μg/ml), equivalent to 10 times the concentration of the working solution (200 μM, that is, 250.2 μg/ml) in the dose group 1.

TABLE 5

NBT positive cell rate (%)

| Sample No. | NBT positive cell rate (%) | Multiple of photo |
|---|---|---|
| 1. NS control group | 6.0 | 200 |
| 2. sp4 200 μM | 80.5 | 200 |
| 3. sp4 100 μM | 75.0 | 200 |
| 4. sp4 50 μM | 73.0 | 200 |
| 5. sp4 25 μM | 70.0 | 200 |

For those skilled in the art, without departing from the scope of the technical solution of the present disclosure, a variety of changes and modifications could be made to the technical solutions or equivalent embodiments of equivalent changes could be made to the present disclosure. Therefore, any simple modification, equivalent change and modification made to the foregoing embodiments according to the technical essence of the present disclosure without departing from the content of the technical solution of the present disclosure should fall within the scope of protection of the present disclosure.

The invention claimed is:

1. A method of treating cancer in a subject, comprising administering to the subject a therapeutically effective amount of a composition, wherein the composition comprises a synthetic peptide sp4 consisting of an amino acid sequence of SEQ ID NO: 1, wherein the cancer is human osteosarcoma or human esophagus cancer.

2. The method according to claim 1, wherein the composition treats tumors in the subject.

3. The method according to claim 1, wherein the composition inhibits proliferation and/or growth and/or invasion of tumor cells.

4. The method according to claim 1, wherein the composition enhances anti-tumor immunoreaction.

5. The method according to claim 1, wherein the composition induces differentiation of tumor cells.

6. The method according to claim 1, wherein the composition inhibits the activity of tumor telomerase.

7. The method according to claim 1, wherein the composition regulates the tumor cell cycle.

8. The method according to claim 1, wherein the subject is a human.

9. The method according to claim 1, wherein the human esophagus cancer comprises malignant tumors of esophageal squamous epithelium and columnar epithelium.

10. The method according to claim 1, wherein the composition is administered by intravenous injection.

11. The method according to claim 1, wherein the synthetic peptide sp4 is administered at a dose of 4-700 mg/kg.

12. The method according to claim 1, the synthetic peptide sp4 is administered at a dose of 4-16 mg/kg.

* * * * *